United States Patent [19]
Azad et al.

[11] Patent Number: 5,614,409
[45] Date of Patent: *Mar. 25, 1997

[54] PRODUCTION OF IBDV VP2 IN HIGHLY IMMUNOGENIC FORM

[75] Inventors: Ahmed A. Azad, Lower Templestowe; Ian G. Macreadie, Templestowe; Neil M. McKern, Lilydale; Paul R. Vaughan, Rowville; Mittur N. Jagadish, Gladstone Park; Kevin J. Fahey, Templestowe; Antony J. Chapman, Murrumbeena; Hans-Georg Heine, Coburg, all of Australia

[73] Assignee: Commonwealth Scientific and Industrial Research Organisation, Campbell, Australia

[ * ] Notice: The term of this patent shall not extend beyond the expiration date of Pat. No. 5,350,575.

[21] Appl. No.: 182,402

[22] Filed: Jan. 18, 1994

Related U.S. Application Data

[63] Continuation of Ser. No. 776,411, Nov. 21, 1991, abandoned.

[30] Foreign Application Priority Data

May 30, 1989 [AU] Australia ................... PJ4469

[51] Int. Cl.$^6$ ........................... C12N 15/81; C12N 15/40; A61K 39/12
[52] U.S. Cl. .................... 435/252.3; 424/192.1; 424/204.1; 435/69.3; 435/320.1; 530/395; 530/403; 536/23.4; 536/23.72
[58] Field of Search ............. 424/184.1, 185.1, 424/193.1, 196.11, 204.1; 530/350, 395, 403; 435/69.3, 320.1, 252.3, 255.1, 240.2; 536/23.4, 23.72

[56] References Cited

U.S. PATENT DOCUMENTS 4,511,652 4/1985 Fogel et al. .................... 435/29
4,940,661 7/1990 Etcheverry et al. .................... 435/69.1
5,350,575 9/1994 Azad et al. .................... 424/192.1

FOREIGN PATENT DOCUMENTS

| 8815845 | 11/1988 | Australia . | |
| 276730 | 8/1988 | European Pat. Off. . | |
| 8502545 | 6/1985 | WIPO | A61K 39/12 |
| 8607060 | 12/1986 | WIPO | C07G 17/00 |
| 8810298 | 12/1988 | WIPO | C12N 15/00 |

OTHER PUBLICATIONS

Jagadish, M.N. et al (1988) Yeast 4:S154.
Azad, A.A. et al. (1986) Virology 149:190–198.
Hudson, P.J. et al. (1986) Nucl. Acids Res. 14:5001–5012.
Fahey, K.J. et al. (1985) J. Gen. Virol. 66:2693–2702.
Miyajima, A. et al. (1985) Gene 37:155–161.
Azad, A. A., et al., Vaccines 90, pp. 59–62 (1990). "Full protection against an immunodepressive viral disease by a recombinant antigen produced in yeast".
Jagadish, M. N., et al., Gene 95:179–186 (1990), "Expression and characterization of infectious bursal viral disease virus polyprotein in yeast".
Hallewell, R. A., et al., Bio/Technology 5:363–366 (1987), "Amino terminal acetylation of authentic human Cu,Zn superoxide dismutase produced in yeast".
MacReadie, I. G., et al., Vaccine 8:549–552 (1990), "Passive protection against infectious bursal virus by viral VP2 expressed in yeast".

Primary Examiner—Thomas M. Cunningham
Attorney, Agent, or Firm—Bacon & Thomas

[57] ABSTRACT

A highly immunogenic form of the VP2 structural protein of IBDV comprises a high molecular weight aggregated form of VP2 produced by the expression of a nucleotide sequence coding for the VP2 structural protein or a polypeptide displaying the antigenicity of all or a part of the VP2 structural protein in a yeast or other eukaryotic host cell.

18 Claims, 16 Drawing Sheets

PRODUCTION OF IBDV VP2 IN HIGHLY IMMUNOGENIC FORM

This application is a continuation of application Ser. No. 07/776,411, filed Nov. 21, 1991, now abandoned.

Infectious Bursal Disease virus (IBDV) is a pathogen of major economic importance to the world's poultry industries. It causes severe immunodeficiency in young chickens by destroying the precursors of antibody-producing B cells in the bursa of Fabricius, one of the two major immunological organs of birds. Young chickens can be passively protected by maternal antibodies deposited in the egg yolk. An inactivated whole virus vaccine is presently used in a vaccination strategy aimed at achieving high levels of maternal antibodies in fertilized eggs to protect the chickens throughout the critical first 4 to 5 weeks after hatching. However, this vaccine is expensive and difficult to produce because the virus has to be grown in the bursae of specific pathogen-free chickens. This also leads to a lot of batch-to-batch variation in virus yields. It is a principal object of the present invention to overcome such problems by the development of a subunit/molecular vaccine based on an isolated vital antigen.

The genome of IBDV has been cloned and sequenced (International Patent Application PCT/AU86/00156), and the probing of the expression products of a range of deletion mutants with a number of virus neutralizing mouse monoclonal antibodies (VN MAbs) has shown that the conformational VN epitope is encoded by a 437 bp AccI-SpeI fragment within the VP2 gene (International Patent Applications PCT/AU86/00156 and PCT/AU88/00206).

It has previously been shown that VP2 expressed as a large β-galactosidase fusion protein in *E. coli* can induce the production of virus-neutralizing and protective antibodies in chicken (International Patent Application PCT/AU88/00206). However, the immunogenicity is very poor, and very large quantities (>1 mg/chicken) of the fusion protein have to be injected in order to elicit the protective immune response. This poor immunogenicity is due to the formation of insoluble inclusion bodies in which the VN epitopes are presumably buried or incorrectly processed or folded, and these inclusion bodies cannot be solubilized and refolded to generate the critical VN epitope. This difficulty of expressing VP2 in a highly immunogenic form is compounded by the conformation dependence and extreme hydrophobicity of the VP2 molecule. It is, therefore, very important to express VP2 in a form in which the VN epitope is both correctly-folded and readily accessible.

Because the expression of VP2 as a large fusion protein as described above resulted in the formation of insoluble inclusion bodies, attempts have been made to express VP2 in an unfused form with the expectation that the soluble expression product would adopt the correct conformation. Using previously available clones in which the five N-terminal amino acids were missing from the VP2 gene sequence, the present inventors were, however, unable to produce unfused VP2 in any significant amount in *E. coli* and none at all in yeast, and this may be due to increased susceptibility of the unfused VP2 molecule to proteolytic degradation.

According to the present invention, there is provided a highly immunogenic form of the VP2 structural protein of IBDV which comprises a high molecular weight aggregated form of VP2 produced by expression of a nucleotide sequence coding for the VP2 structural protein or a polypeptide displaying the antigenicity of all or a part of the VP2 structural protein.

Preferably, the high molecular weight aggregated form of VP2 is produced by expression of an appropriate nucleotide sequence in yeast, for example in *Saccharomyces cerevisiae* or *Kluyveromyces lactis*, or another eukaryotic host cell.

Preferably also, the nucleotide sequence is one which is expressed as a VP2 construct having a short N-terminal fusion, for example a construct in which the five N-terminal amino acids of native VP2 have been restored, or constructs in which these amino acids have been replaced by an octapeptide sequence such as MNSSSVPG (for construct expressed in *E. coli*) or MFSELDPQ (for construct expressed in yeast).

In another aspect, the present invention provides a vaccine composition for stimulating an immune response against IBDV, which comprises the highly immunogenic form of the VP2 structural protein of IBDV as described above, together with an acceptable carrier therefor. Optionally, the composition may also comprise an adjuvant.

The invention also extends to a method for the preparation of this highly immunogenic form of VP2, which comprises expression of an appropriate nucleotide sequence, particularly in yeast, as well as to recombinant DNA molecules, recombinant DNA cloning vehicles or vectors and host cells (including yeast cells) as broadly described in International Patent Application No. PCT/AU86/00156, which comprise a nucleotide sequence which is capable of being expressed as this highly immunogenic form of VP2.

The five N-terminal amino acids of the VP2 molecule are not present in VP2 constructs such as clone PO described in International Patent Applications Nos. PCT/AU86/00156 and PCT/AU88/00206. Expression of the PO insert in certain *E. coli* expression vectors and yeast expression vector pAAH5 (obtained from Dr. B. D. Hall, University of Washington, Seattle, U.S.A.) which should give rise to unfused VP2, did not result in stable synthesis of VP2 protein. It has now been found that replacement of these N-terminal amino acids with a small N-terminal fusion or the restoration of the "native" or "near native" N-terminus is sufficient to stabilize the recombinant VP2, and therefore, leads to higher yields. The inclusion of a short N-terminal fusion sequence is preferred, as it was found that the longer the N-terminal fusion the greater is the tendency to form insoluble inclusion bodies. The addition of only eight amino acids, from the multiple cloning site of expression vector pTTQ18 (Amersham), at the N-terminus stabilized the expression of VP2 in *E. coli*. Similar results were obtained in yeast when eight amino acids from the N-terminus of the CUP1 gene product (for intracellular production), or the pre-pro sequence of MFα1 gene product (for extracellular production) were added to the N-terminus of VP2. These results show that very small N-terminal fusions are sufficient for the stabilization of the VP2 expression products in both *E. coli* and yeast. Further, addition of the sequence MSLNS, a "near native" sequence that differs from the "native" or wild-type N-terminal sequence MTLNS at only the second position, resulted in stable synthesis of unfused VP2 in yeast. Other sequences with similar structural properties should also provide N-terminal stability to VP2.

About 60–80 percent of the VP2 produced with small N-terminal fusion remained in the supernatant when the bacterial or yeast lysates were spun at 12,000 rpm. Most of the remaining VP2 was associated with membranous material present in the 12,000 rpm pellet. In *E. coli*, there was evidence of small amounts of inclusion bodies also being formed. Some non-ionic detergents selectively removed membrane proteins from the 12,000 rpm pellets but did not solubilize the VP2 present in the pellet.

The recombinant VP2 contained in yeast cell lysates, when injected into chickens, induced high titres of antibody which neutralized the infectivity of IBDV in cell-cultures, reacted with the virus in the ELISA, and when injected into young chickens, conferred passive protection against infection. More particularly, eggs laid by vaccinated hens were found to contain high titres of antibody to IBDV in their yolk, and the chickens hatched from fertile eggs from vaccinated hens had high titres of circulating maternal antibodies. The level of maternal antibody was sufficient to protect some of the chickens for up to 3 weeks after hatching, against an intraocular challenge with 100 times an infectious dose of IBDV (002/73).

The minimum protective titres of maternal antibody in the circulation of progeny from hens vaccinated with recombinant VP2 were similar to those reported for maternal antibodies to whole IBDV (Fahey et.al., 1987). This indicated that the protective ability of antibodies to recombinant VP2 were similar to antibodies to the original intact virus. Studies on the decline in the titre of maternal antibodies to recombinant VP2 in progeny chickens showed that it had a half life of 6 days, which is similar to that reported previously for the half ,life of antibodies to the original intact virus (Fahey et.al., 1987).

When recombinant VP2 vaccine was injected into adult hens which had previously been primed (sensitized) by exposure to the live virus, it induced an anamnestic serum antibody response, both of virus neutralizing and ELISA antibody.

Further features of the present invention are described in the following Examples, and in the accompanying drawings. In the Examples, standard techniques were used as described in well known texts, including Maniatis et.al. "Molecular Cloning; A Laboratory Manual", (1982) Cold Spring Harbor. Restriction enzymes were used in accordance with manufacturer's instructions.

In the drawings:

FIG. 1 shows the construction of yeast and *E. coli* vectors for the expression of IBDV antigens. A. Schematic representation of the IBDV polyprotein sequence in clone pEX.PO (described in PCT/AU86/00156). Square blocks depict repeats of the pentapeptide sequence AXAAS that occur four times in the polyprotein. B. The vector pYELC5 employed for the copper inducible expression of foreign proteins in yeast. C. Expression clones for the production of IBDV antigens. (i) clone pYELC5.PO was constructed by inserting a SmaI-PstI fragment (3.0 kb) encoding the IBDV polyprotein into pYELC5 cut with PvuII and PstI. (ii) Clone pYELC5.POΔXhoI was constructed by deleting the XhoI fragment from pYELC5.PO. This removes all the IBDV sequences downstream of the XhoI site including the translation stop codon at the C-terminus of the polyprotein, as well as the CUP1 a downstream sequences including the CUP1 transcription terminator. The next in-phase translation stop codon is present about 0.3 kb downstream of the XhoI site resulting in the addition of ca. 12 KDa of irrelevant protein at the C-terminus of VP2. (iii) A refinement of pYELC5.POΔXhoI in which translation is stopped shortly after the AXAAS is pYELC5.POΔT. This construct has an oligonucleotide translation terminator inserted into the XhoI site of pYELC5.POΔXhoI. In Western blots with MAb 9/6, a single product the size of IBDV VP2 a (ca 41 kD; Azad et.al., 1987) is seen in a lightly loaded gel. The translation product is expected to differ from that of pYELC5.VP2T (see below) by having 3 fewer amino acids (RIH) at the C-terminus. Translation in pYELC5.POΔT is designed to terminate immediately after the AX (actually AR) of the second AXAAS. (iv) other constructs derive from pYELC5.VP2 J, constructed by the insertion of the SmaI-XhoI fragment into the PvuII-SalI sites of pYELC5. This construct has a yeast CUP1 transcription terminator but translation stops some 65 codons downstream from the second AXAAS. (v and vi) The missense translation in pYELC5.VP2 J has been overcome by two strategies. pYELC5.VP2 J has been cleaved with PstI and then the 3' overhanging ends have been removed by treatment with T4 polymerase in the presence of dNTPs. The religation of this produces pYELC5.VP2T (v) and in this vector translation is terminated much earlier, almost immediately downstream of the second AXAAS sequence. When religation is performed in the presence of the oligonucleotide dCGGATCCG the downstream CUP1 sequences can be brought into frame generating pYELC5.VP2 C (vi). This results in a metallothionein fusion to VP2. D. The *E. coli* expression clone pTTQ18.VP2 was constructed by inserting a SmaI-XbaI fragment from clone pEX.PO ΔXhoI-PstI (PCT/AU88/00206) into the vector pTTQ18 (Pharmacia) cut with SmaI and XbaI.

FIG. 2 shows the cloning strategy for the six yeast expression constructs described in FIG. 1.

FIG. 3 shows Western blots of IBDV antigens produced by yeast transformants. Proteins were Western blotted in duplicate. Filter A was probed with anti-VP2 MAb 9/6 and filter B was probed with anti-VP3 MAb 17/80. The protein bands were visualized by reacting the filters with goat anti-mouse IgG horse radish peroxidase conjugate (Bio-Rad) followed by HRP colour developing reagent as described by Bio-Rad. Proteins displayed are from yeast transformed with vectors pYELC5 (lane 1), pYELC5.PO (lane 2), pYELCR.POΔXhoI (lane 3), pYELC5.VP2T (lane 4) and from IBDV (lane 5). Pre-stained molecular weight markers are in lane M. The arrows pointing to filter A indicate the positions of VP2a (41 kDa) and VP2b (37 kDa), and the arrow pointing to filter B indicates the position of VP3 (32 kDa). The polypeptide bands (lane 2) larger than VP2a on filter A and VP3 on filter B respectively, represent incomplete cleavage of the precursor polyprotein expressed from the large genomic segment in clone pYELC5.PO.

FIG. 4 shows gel-filtration of pYELC5.PO lysate on Sephacryl S.300 column. The top panel shows reactivity of column fractions with various MAbs; ●—● anti-VP3 MAb 17/80; ▲—▲ VN MAb 9/6; ■—■ VN MAb 39A. The bottom panel shows the $A_{280}$ profile (solid line) and the amount of protein present in different fractions (●---●). ○—○ proteolytic activity measured at $A_{595}$ nm of supernatant containing soluble peptides released following incubation of samples with Remazol Blue dye conjugated to hide powder.

FIG. 5 shows gel-filtration of pTTQ18.VP2 lysate on Sephacryl S.300 column. The top panel shows reactivity with VN MAbs 9/6 (▲—▲) and 39A (■—■). The bottom panel shows the A280 profile (solid line) and the amount of protein in individual fractions (●---●).

FIG. 6 shows serum antibody responses of adult hens vaccinated with inactivated native VP2a/2b or either of two recombinant subunit vaccines. Groups of 4 hens were inoculated i.m. with either 20 μG VP2a/2b or 45 μg of either pYELC.5-PO or pYELC.5-VP2 in Freund's incomplete adjuvant. The recombinant proteins were the resuspended 40K pellets from the S300 void volume fractions of 12K supernates of each yeast cell lysate. A: ELISA titres; B: Virus neutralization titres.

FIG. 7 shows Western blot analyses of the VP2 present in the void volume (tubes 45–55) and included volume (tubes 81–90) fractions of yeast and E. coli lysates subjected to Gel-filtration (FIGS. 3 and 4). Samples analysed were: 1. pYELC5.PO; 2. pYELC5.POΔXhoI; 3.pYELC5.VP2T; 4. pTTQ18.VP2. a and b represent protein present in the void volume and included volume fractions, respectively. Filter A was probed with anti-VP2 MAb 9/6 and filter B was probed with anti-VP3 MAb 17/80.

Figure 1:
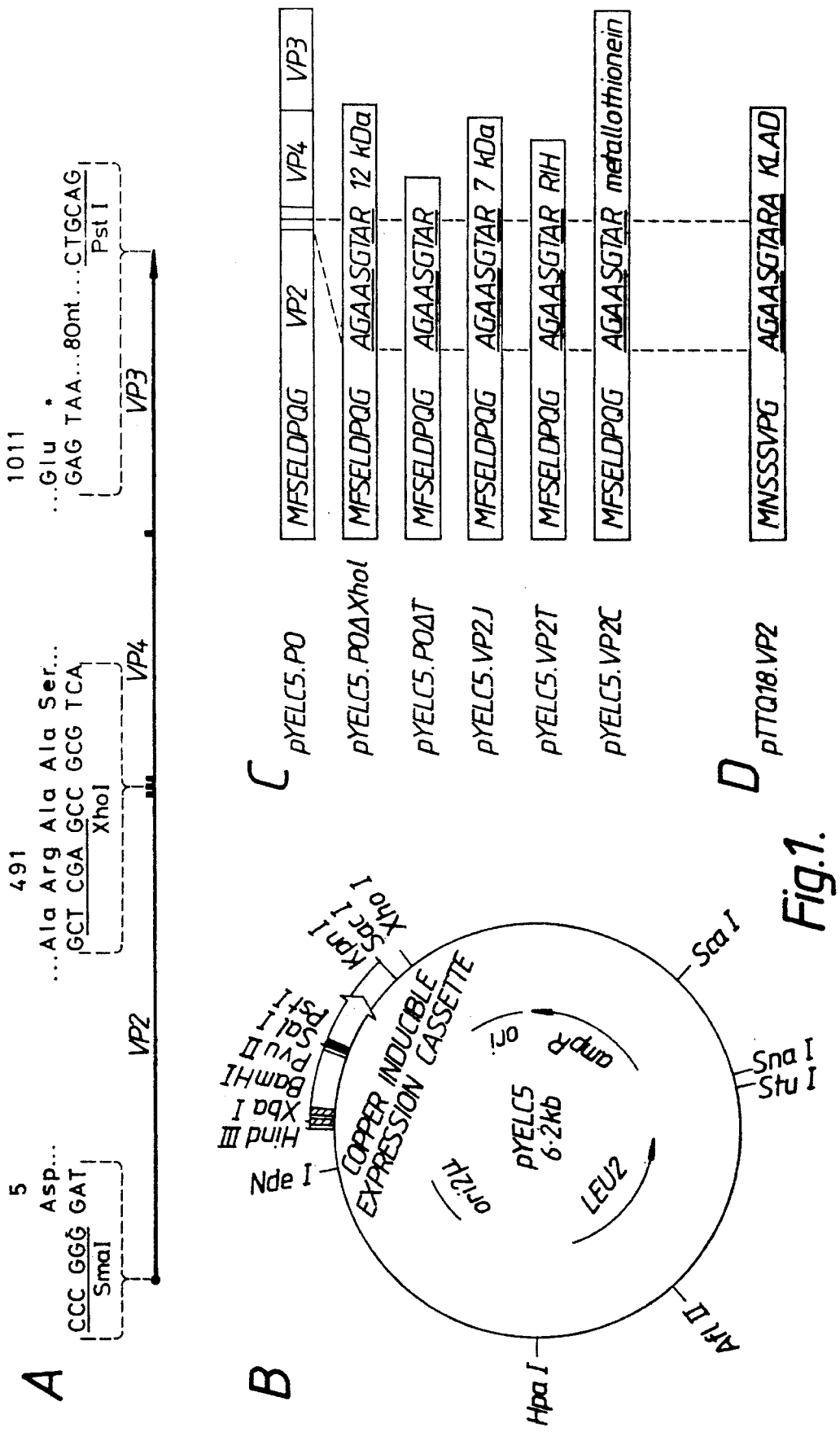

The complimentary DNA obtained from genomic RNA using oligonucleotide N527 in reaction A (wells, 1, 3, 5, 8) or oligonucleotide N526 in reaction B (wells 2, 4, 6, 9), was used as template in PCR amplification with primers N526 and N527 (wells 1, 2, 5, 6, 7) or with primers N528 and N533 (wells 2, 3) or without primers (wells 8, 9). The molecular weight marker in well 10 is Digrest (Pharmacia). For the PCR amplification in wells 5 and 6 a different PCR buffer has been used than in wells 1 and 2.

FIG. 11 shows construction and maps of plasmids.

A. pIP41:

VP2 (of strain 002-73) was subcloned as a 1.5 kb SmaI-XbaI fragment from plasmid pEX.POΔXhoI-PstI into the SmaI-XbaI sites of pTTQ18 (Amersham) to give pTTQ18-VP2. The small DraI-SalI fragment was then deleted to remove the lacZa fragment and a 12-mer BamHi linker (Pharmacia) and the f1 intergenic region from pUC-f1 (Pharmacia) were inserted at that position to give pIP41. Expression of VP2 is under control of the tac promoter and single stranded DNA can be obtained using M13 helper phage.

B. pIP201:

The EcoRI-XhoI fragment of pIP41 containing VP2 of strain 002-73 has been replaced by the homologous region from variant strain E, obtained by PCR amplification of genomic RNA.

C. pIP207:

The small SacI fragment of pIP201 containing the C-terminal half of VP2 has been replaced by the homologous fragment from pIP41. The VP2 hybrid protein consists of a N-terminal half from variant E fused to the C-terminal half from strain 002-73.

D. Yeast expression vector pIP211:

The SacI-XhoI fragment of pYELC5.POΔXhoI containing the C-terminal half of VP2 has been replaced by the homologous fragment of pIP201. This gives rise to a VP2 hybrid consisting of the N-terminal half from strain 002-73 and the C-terminal half from variant strain E.

Figure 12:
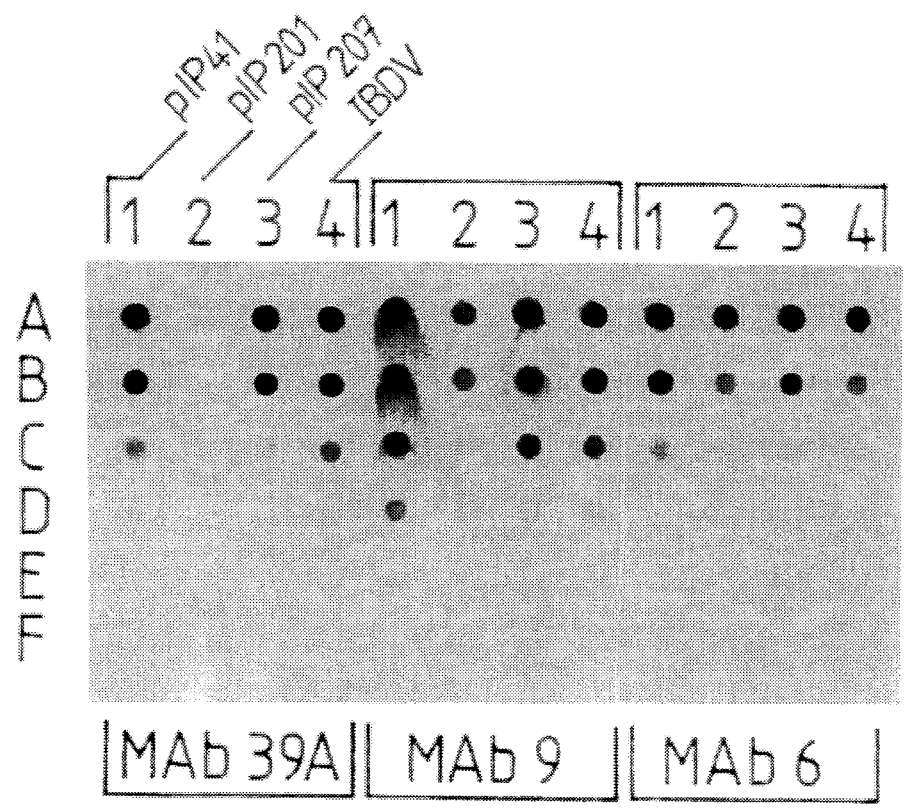

FIG. 12 shows dot blots of E. coli lysates with monoclonal antibodies.

The 3K supernatants of E. coli lysates were adjusted to identical protein concentrations and 1:5 dilutions (A to F) were loaded onto dot blots. The lysates from pIP41, pIP201, pIP207 and 5 μg IBDV viral proteins were analysed in dot blots with MAb39A, MAb9/6 and MAb6/1 as indicated.

Figure 13A:
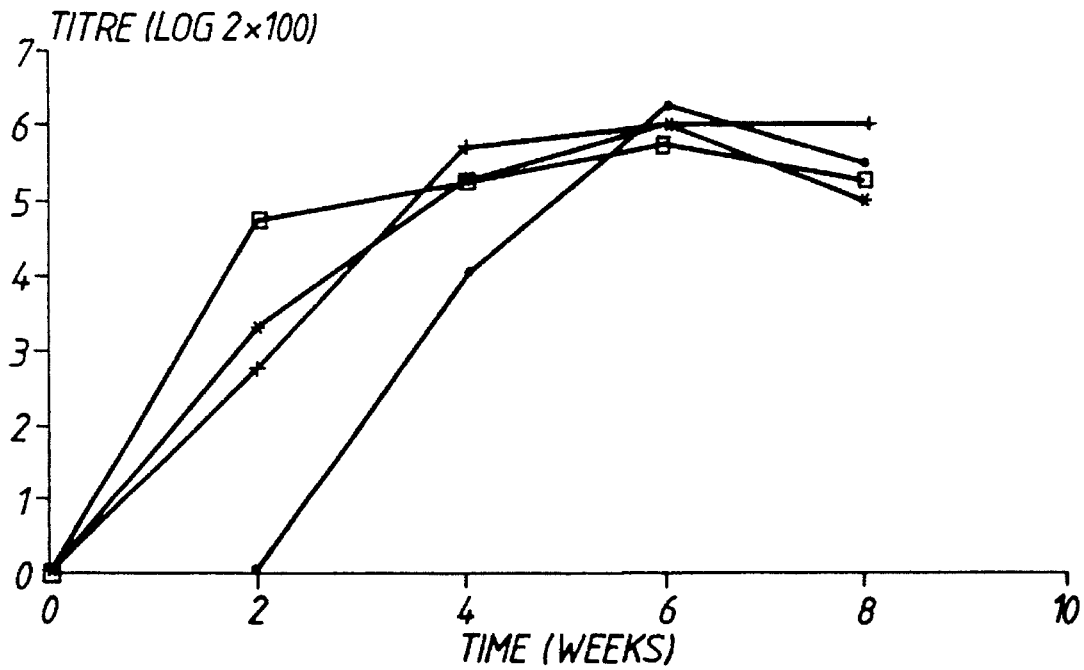
Figure 13B:
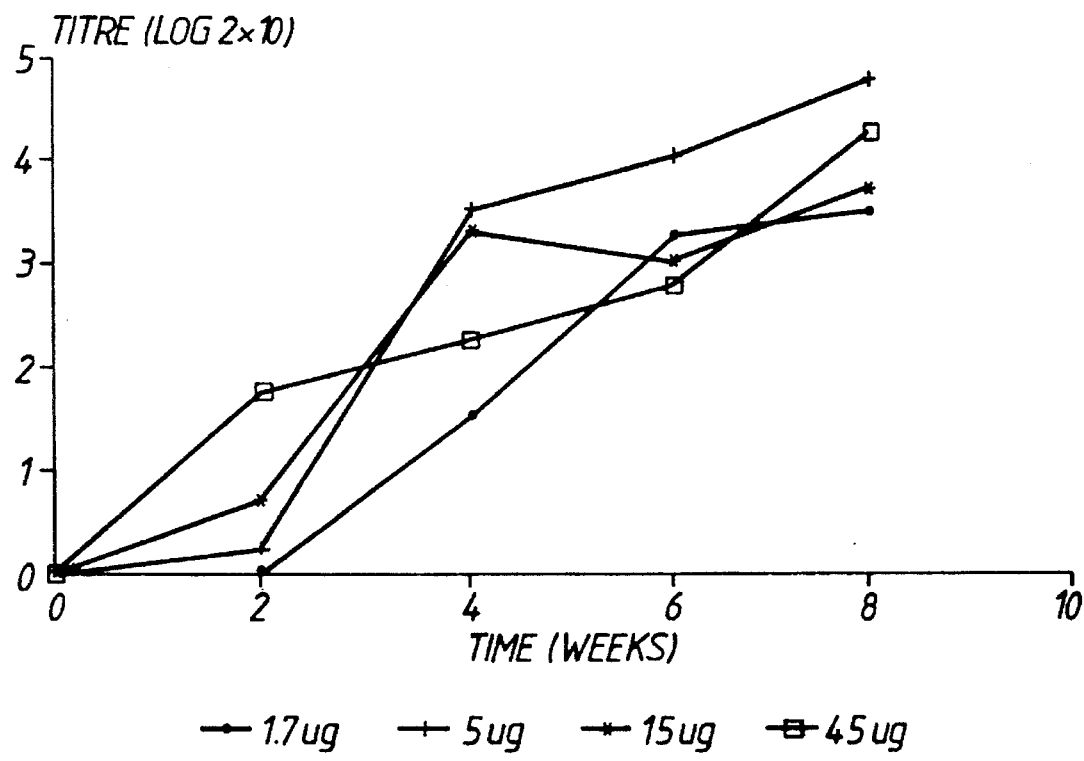

FIG. 13 shows the dose response of adult chickens of pYELC5-VP2 in Freund's incomplete adjuvant. The serum was assayed for the titre of ELISA (A) and virus neutralizing (B) antibody.

Figure 14:
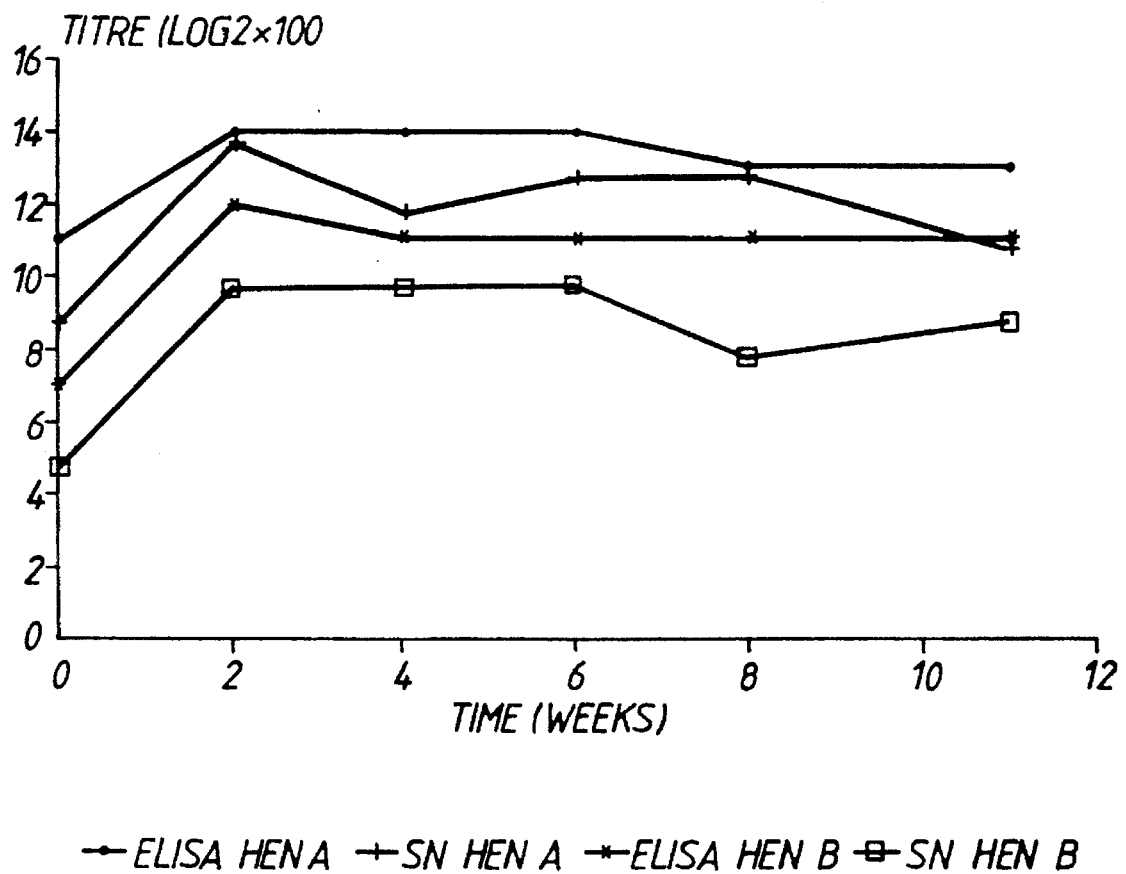

FIG. 14 shows the serum antibody response of two primed adult hens to 45 μg of pYELC5-VP2 in Freund's incomplete adjuvant. The serum was assayed for the titre of ELISA (A) and virus neutralizing (B) antibody.

EXAMPLE 1

Immunoloqical characterization of E.coli derived VP2 with small N-terminal fusion.

A large number of VP2 constructs with various lengths of N-terminal fusions have been produced in E. coli, and it was found that the degree of insolubility due to formation of inclusion bodies tended to increase with increase in length of N-terminal fusion. The construct pTTQ18.VP2 (see FIG. 1D) in which the five N-terminal amino acids of VP2 were replaced with eight amino acids MNSSSVPG from the pTTQ18 vector, was found to be the most suitable as the expression levels were reasonably high, the product was very stable, and up to 80 percent remained in the 12,000 rpm supernatant. It reacts very strongly with a large number of VN MAbs (described in International Patent Application PCT/AU88/00206). On Western blots, it reacts with anti-VP2 MAbs that recognize denatured VP2. Under non-denaturing conditions, it reacts strongly with VN MAb 39A that only recognizes the conformational epitope suggesting that at least part of the molecule is correctly folded. Construct pTTQ18.VP2 is also immunoprecipitated with a large number of VN MAbs. As shown in Table 1, when injected into chickens it produces anti-VP2 antibodies, however the antibodies do not neutralize the virus to any significant extent. This situation did not improve when immunostimulating complexes (ISCOMS) were made from the E. coli derived VP2.

TABLE 1

| Testing serum from SPF chickens six weeks after immunisation with pTTQ18 VP2 | | |
|---|---|---|
| CHICKEN | EIA TITRE | VN TITRE |
| A | 3200 | <80 |
| D | 1600 | <80 |

EXAMPLE 2

Immunological characterization of yeast-derived VP2

Figure 2I:
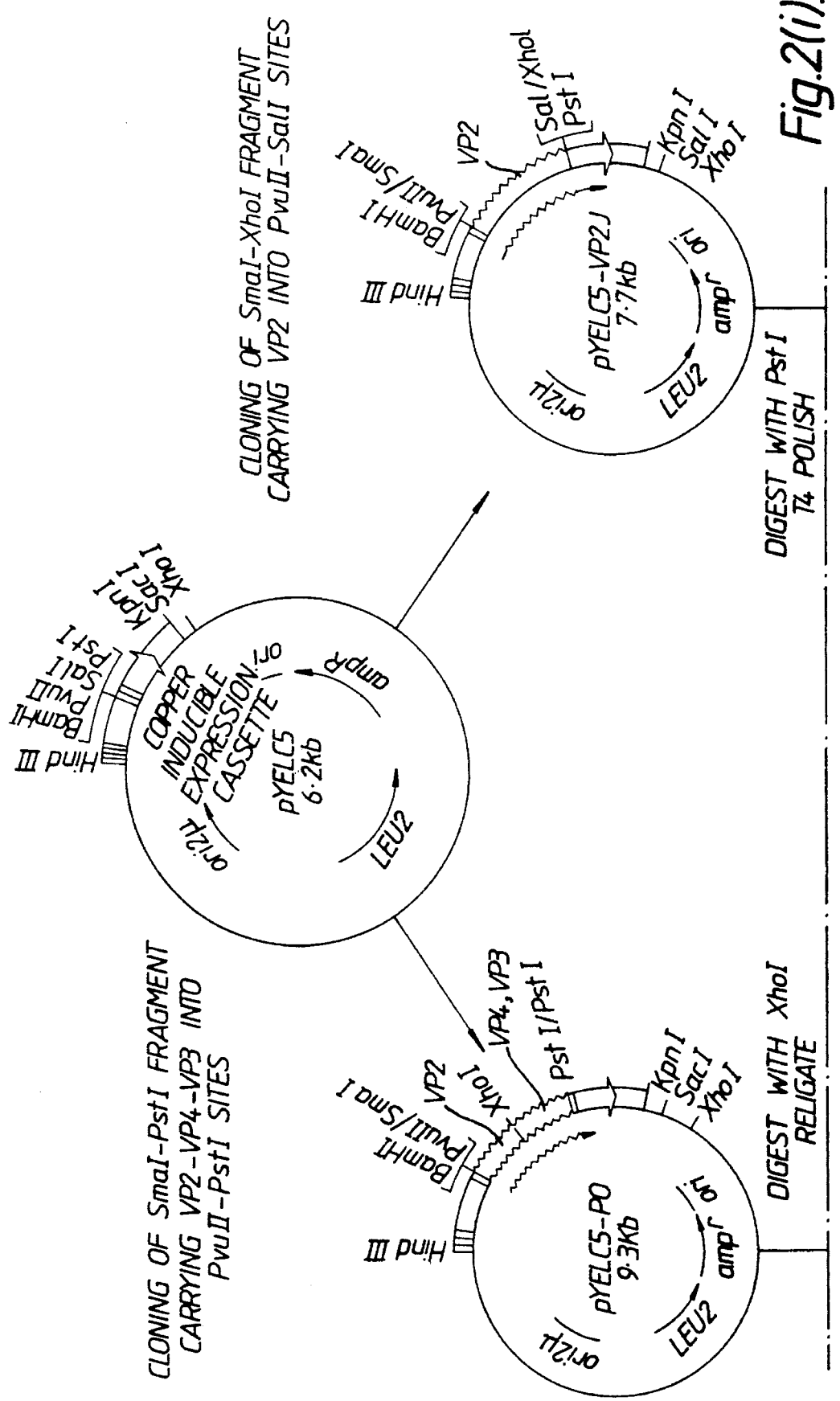
Figure 2:
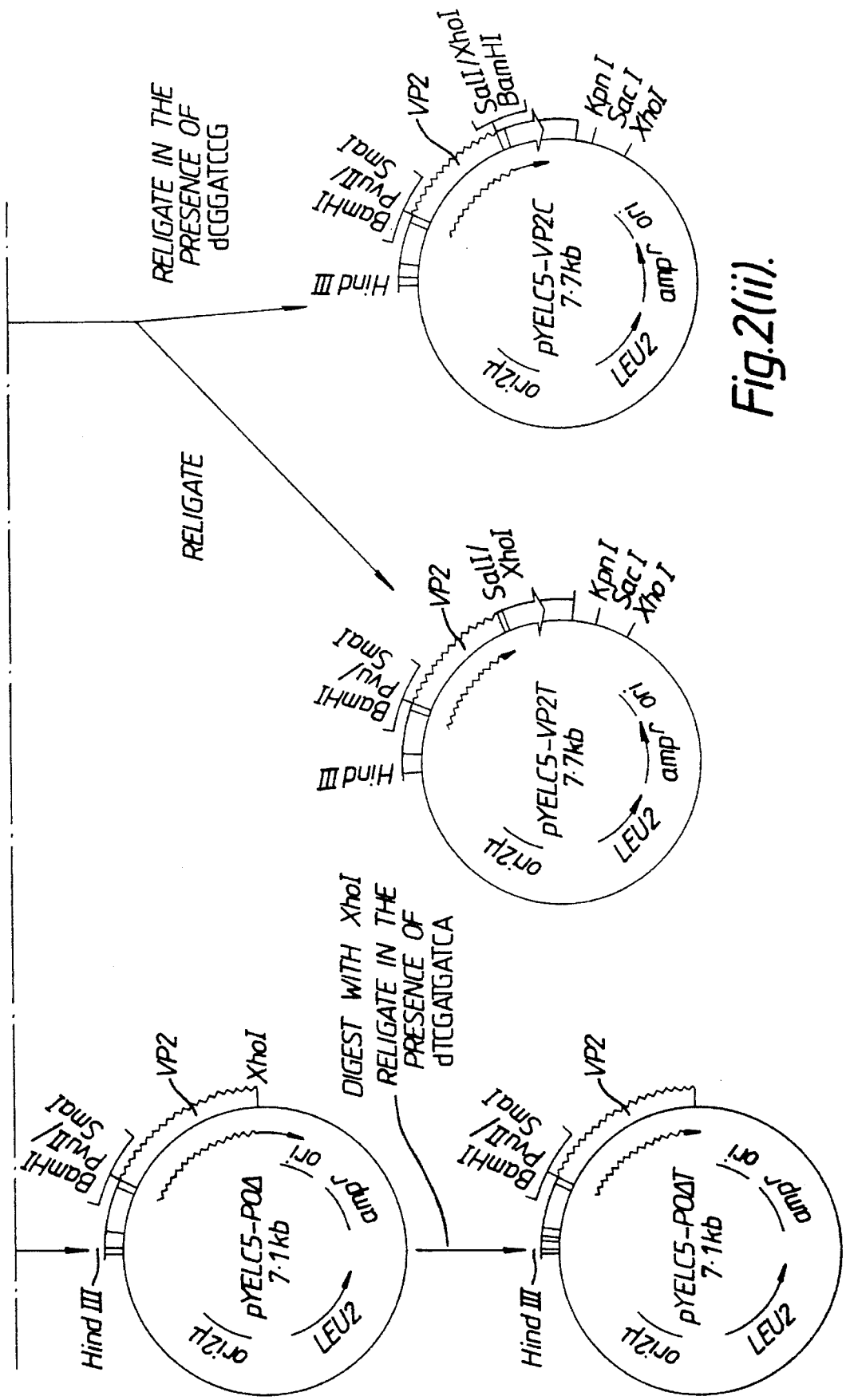

The yeast constructs are shown in FIG. 1C and the cloning strategy is set out in FIG. 2. The VP2 expressed in *Saccharomyces cerevisiae* has been produced using the copper-inducible expression vector pYELC5 (see FIG. 1B; Australian Patent Application 15845/88), and the *Klurveromyces lactis* construct has been produced using the *K.lactis* vector E1 (kindly supplied by Dr. D. Clark-Walker, Australian National University, Canberra, Australia). In all the yeast constructs, the 5 N-terminal amino acids of VP2 were replaced by an octapeptide MFSELDPQ derived from the N-terminus of the yeast CUP1 gene product. The pYELC5.PO construct contains the entire large segment of the IBDV genome which encodes a precursor polyprotein. In yeast, as in E. coli, the precursor polyprotein is cleaved to give rise to VP2, VP3 and VP4. The CUP1 octapeptide is present at the N-terminus of the cleaved VP2 molecule. The VP2 molecule produced in clone pYELC5.POΔXhoI contains an additional 12 KDa of 'irrelevant' protein at the C-terminus. The 'irrelevant' protein is not present in VP2 produced in clone pYELC5.VP2T in which a translational stop codon has been introduced at the C-terminus of the VP2 molecule. The *K.lactis* VP2T has the same insert as in pYELC5.VP2T.

Figure 3A:
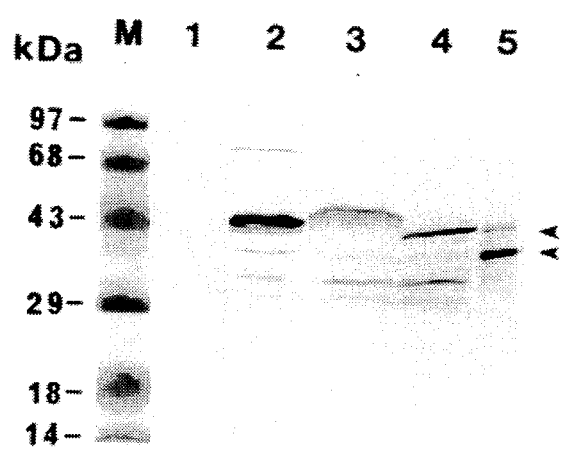
Figure 3B:
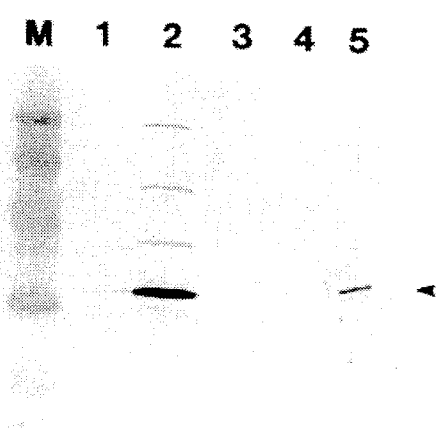

Western blots of the expression products probed with the anti-VP2 MAb 9/6, and anti-VP3 MAb 17/80 show (FIG.3) that the expression of the large genomic segment of IBDV (.clone pYELC5.PO) in yeast results in the. production of correctly processed VP2 and VP3 from the precursor polyprotein as found in *E. coli* and cell-free translation systems. As expected, VP3 is not produced in clones pYELC5.POΔXhoI and pYELC5.VP2T because of the deletion of the VP4 and VP3 encoding regions (FIG.1). The VP2 molecule produced in pYELC5.POΔXhoI has an additional 12 KDa of irrelevant protein at the C-terminus and has a slower electrophoretic mobility than the correct-sized VP2 produced in clone pYELC5.VP2T in which a translation stop codon has been introduced at the C-terminus. The bands appearing below VP2a are degradation products.

In order to assess immunogenicity, antibodies were raised against the yeast-derived IBDV antigens by a single intramuscular injection of the yeast lysate, 12K rpm supernatant, or column-derived fractions (equivalent in reactivity on serial dot blots with VN MAbs to 50 micrograms of viral VP2), in Freund's incomplete adjuvant into unprimed SPF chickens in duplicate. All the yeast constructs have in vitro antigenic properties identical to that of native VP2 and the *E.coli* construct pTTQ18.VP2. When they are emulsified in adjuvant and injected into chickens they produce very significant ELISA and VN titres (Table 2), and the sera from the inoculated birds are able to passively protect young chickens from IBDV infection (Table 3). Thus, the yeast-derived VP2, is immunogenically very similar to native viral VP2, in that it induces a protective antibody response in chickens.

TABLE 2

Testing serum from SPF chickens six weeks after immunisation with either viral VP2 or recombinant IBDV yeast constructs

| CONSTRUCT | EIA TITRE | VN TITRE |
| --- | --- | --- |
| pYELC5.PO(a) | 51,200 | 2560–5120 |
|  | 102,400 | >5120 |
| pYELC.5.POΔXhoI(a) | 51,200 | 25,600 |
|  | 51,200 | 25,600 |
| pYELC5.VP2T(b) | 12,800 | 1,280 |
|  | 25,600 | 5,120 |
| K. lactis VP2T(a) | 25,600 | 2,560 |
|  | 121800 | 1,280 |
| pYELC5.POΔT(a) | 3,200 | 320 |
| VIRAL VP2 | 51,200 | 25,600 |
|  | 51,200 | 51,200 |

(a)3K/12K supernatant
(b)Sephacryl S-300 void volume 40K pellet
NT = not tested

TABLE 3

Passive protection of three day-old SPF chickens, from challenge with 100 CID$_{50}$ IBDV, by intraperitoneal administration of immune chicken serum.

| CHICKEN SERUM AGAINST | NO. OF CHICKENS PROTECTED |
| --- | --- |
| Preimmune serum (control) | 0/5 |
| pYELC5.PO | 5/5 |
| pYELC5.POΔXhoI | 5/5 |

TABLE 3-continued

Passive protection of three day-old SPF chickens, from challenge with 100 CID$_{50}$ IBDV, by intraperitoneal administration of immune chicken serum.

| CHICKEN SERUM AGAINST | NO. OF CHICKENS PROTECTED |
| --- | --- |
| pYELC5.VP2T | 5/5 |
| K. lactis VP2T | 5/5 |
| IBDV | 5/5 |
| VIRAL VP2 | 5/5 |

NT = not tested

EXAMPLE 3

Gel-filtration and sedimentation of yeast- and *E.coli* derived VP2.

Figure 4:
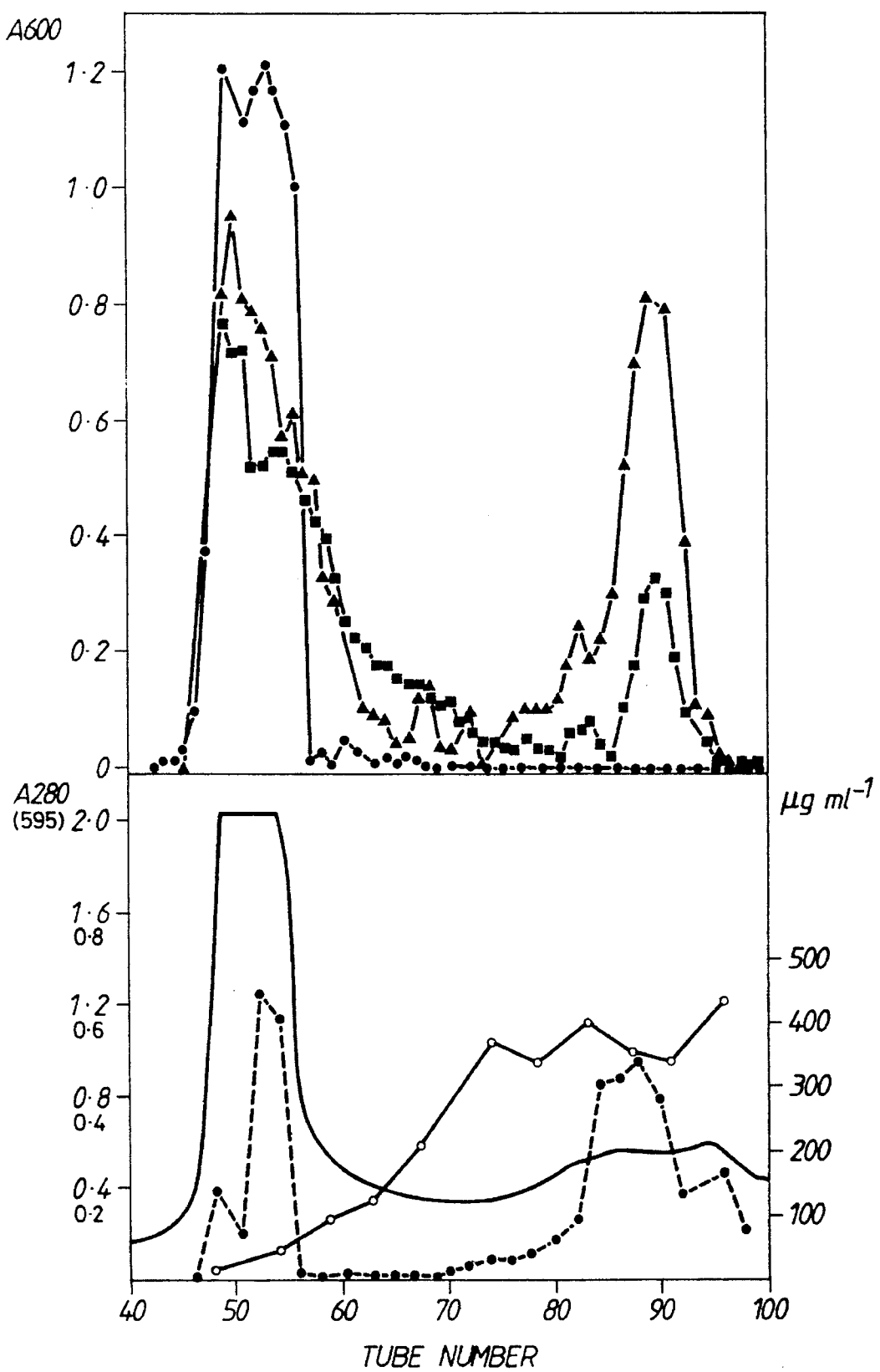
Figure 5:
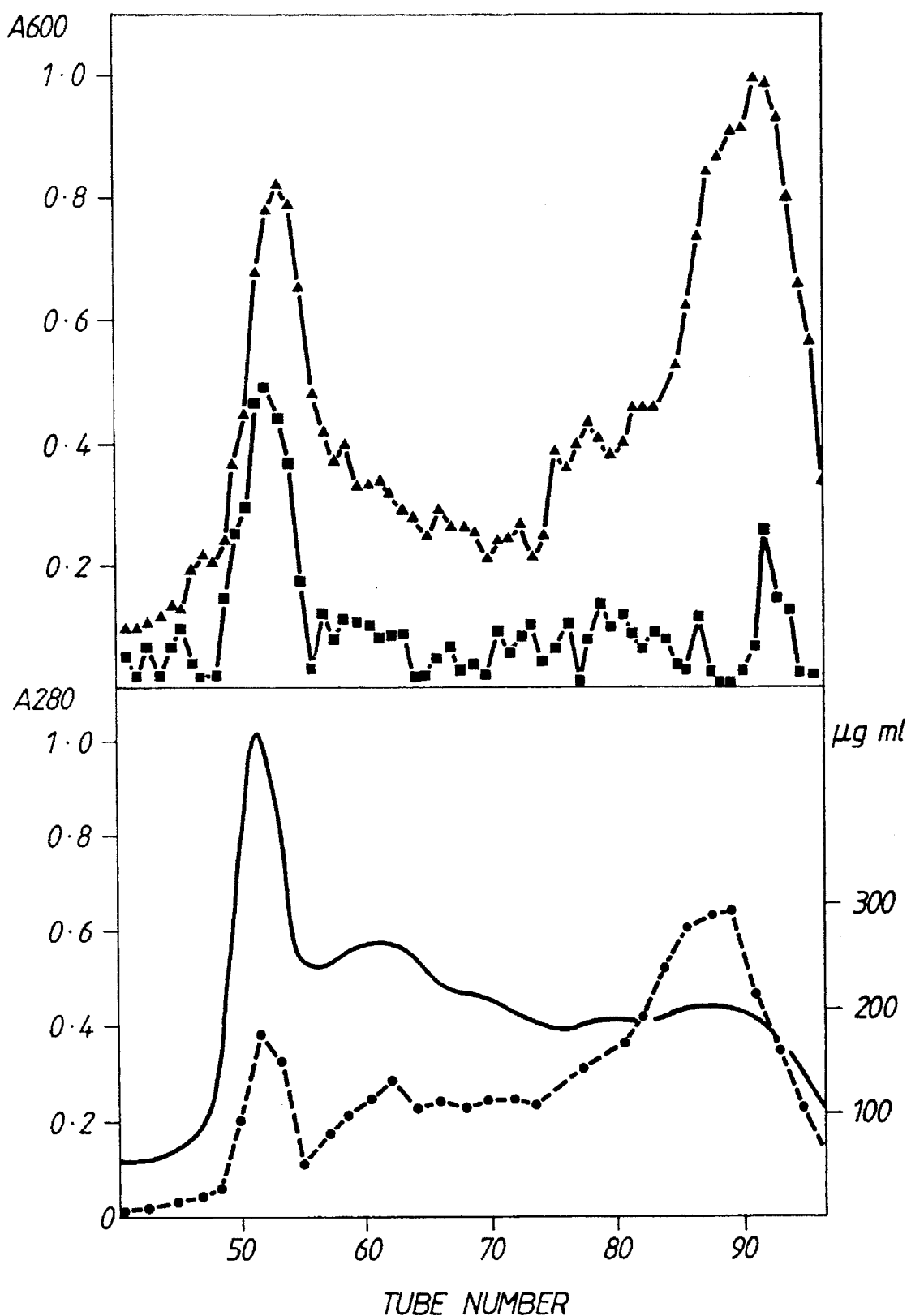

When the 12,000 rpm supernatants of the *E. coli* pTTQ18.VP2 or the yeast VP2 constructs were subjected to gel filtration on Sephacryl S-300 column, the VP2 eluted in two distinct fractions (FIGS. 4 and 5). There was a big peak in the void volume which is very milky in appearance in yeast and less so in *E. coli*, and which contains very little protein. The column fractions were dot-blotted onto nitrocellulose filter and probed with various monoclonal antibodies to localize the IBDV antigens. The anti-VP3 MAb 17/80, as expected, reacts only with material from clone pYELC5.PO as this is the only clone which contains IBDV genetic material other than the VP2 gene. The reaction is confined to the void volume fractions. VN MAb 9, which recognizes undenatured and denatured VP2, reacts with both the void volume and included volume fractions of the yeast constructs pYELC5.PO (FIG. 4), pYELC5.POΔXhoI, pYELC5.VP2T, *K.lactis* VP2T (result not shown), and the *E. coli* construct pTTQ18, VP2 (FIG. 5). VN MAb 39A, which only recognizes undenatured VP2, reacts predominantly with the void volume fractions from all the above constructs suggesting that more of the correctly-folded molecules are present in the void volume.

Figure 6A:
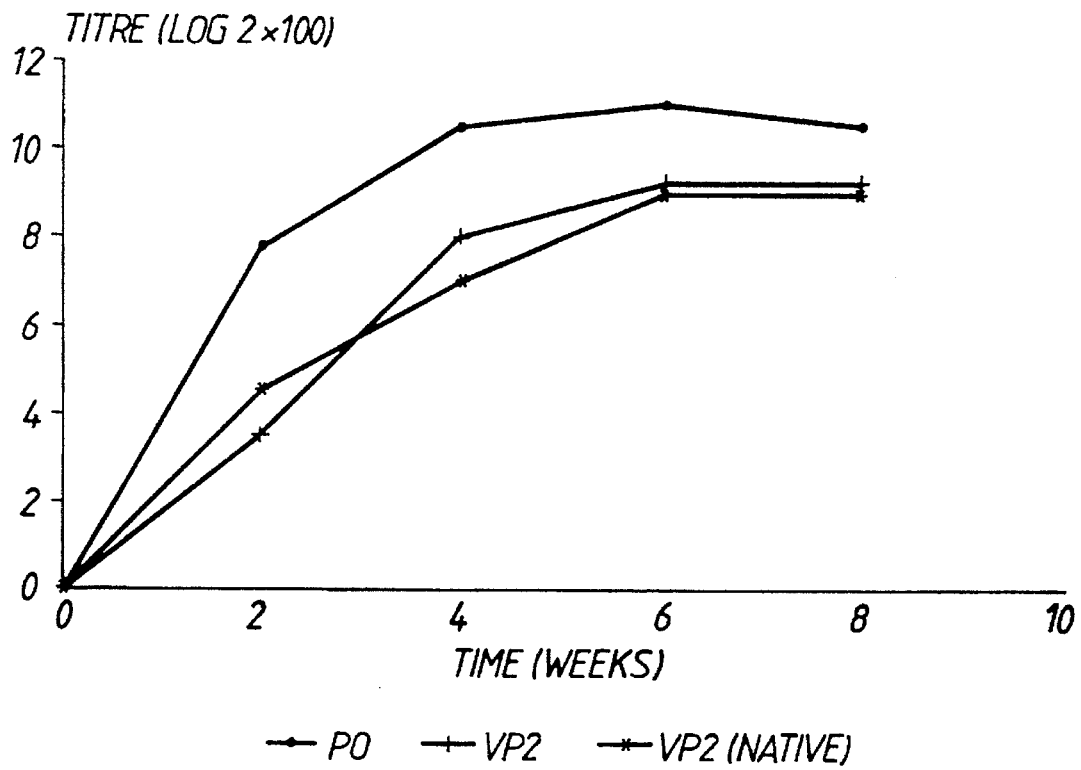
Figure 6B:
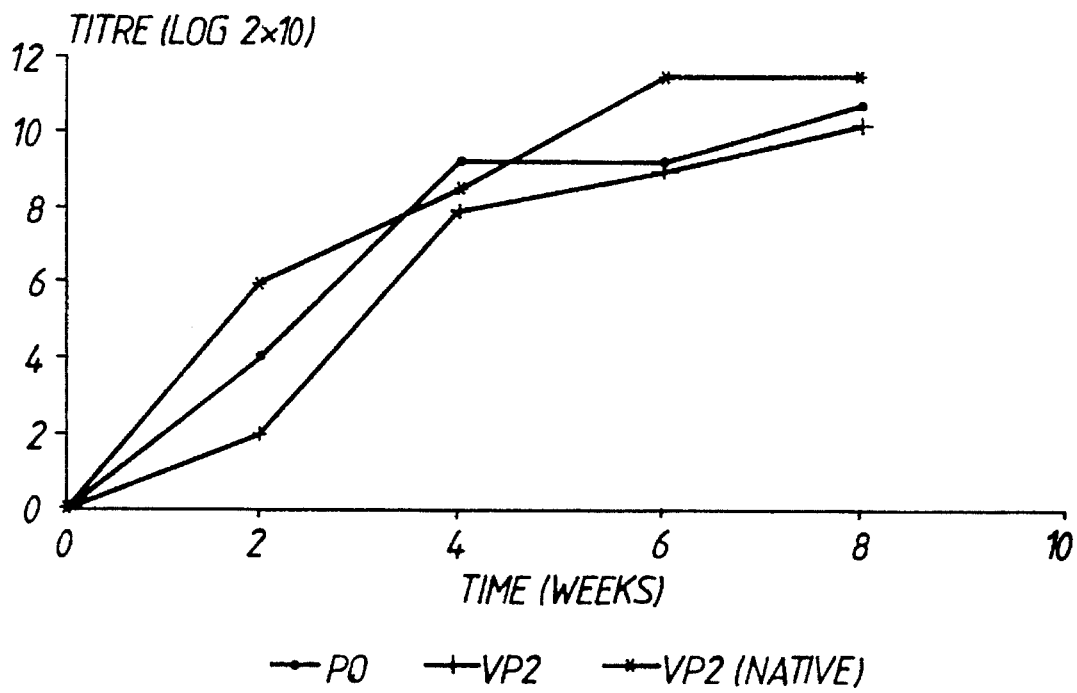

In all the yeast constructs and in pTTQ18.VP2, the VP2 present in the void volume quantitatively sediments when spun at 40,000 rpm for one hour. The VP2 present in the included volume does not sediment under similar conditions. This suggests that the VP2 eluting in the void volume is present in a high molecular weight aggregated form. In clone pYELC5.PO, both VP2 and VP3 are present in the void volume, and about 50% of the VP3 co-sediments with VP2 on high speed centrifugation. Void volume material immunoprecipitated with anti-VP3 MAb does not react with anti-VP2 MAbs on Western blots, and material precipitated with anti-VP2 MAb does not react with anti-VP3 MAb (results not shown). This would indicate that in pYELC5.PO, the VP2 and VP3 present in the void volume are not complexed to each other. The 40,000 rpm pellet of the void volume fraction of pYELC5.PO, contains both VP2 and VP3, but this pellet is no more immunogenic than 40,000 rpm pellets obtained from the other yeast constructs (FIG. 6a, 6b). This supports the earlier disclosure that VP2 is the major host-protective antigen of IBDV (PCT/AU86/00156) and PCT/AU88/00206).

Electron micrographs of the void volume material do not show any defined particulate structures, but do form irregular dense bodies that specifically bind VN MAbs and immunogold particles (results not shown).

EXAMPLE 4

Western blot analyses of VP2 and VP3 fractionated by gel filtration.

Figure 7A:
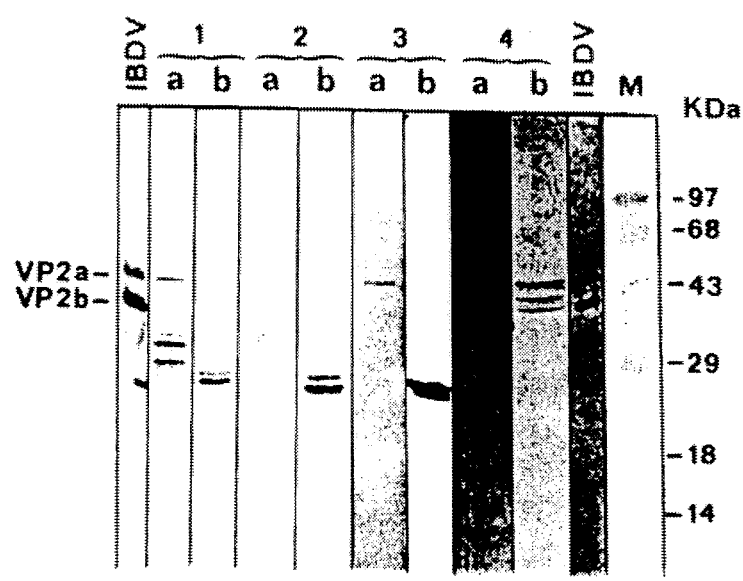
Figure 7B:
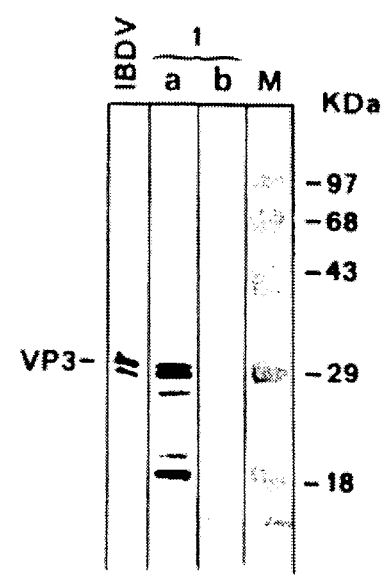

The Western blots of the Sephacryl S-300 column fractionated yeast in *E. coli* constructs are shown in FIG. 7. The void volume fraction of the *E. coli* pTTQ18.VP2 contains totally undegraded VP2, while the included volume fractions contained some degraded material (FIG. 7). The void volume fractions of pYELC5.PO and pYELC5.VP2T and *K.lactis* VP2T contain a prominent 41 kDa band corresponding to VP2 a, and in pYELC5.POΔXhoI a band about 12 kDa larger than VP2a because of the presence of 'irrelevant' *E. coli* sequence at the C-terminus. Various amounts of degraded VP2 are also present in the void volume of all the yeast constructs. The extent of breakdown is least pronounced in pYELC5.VP2T and *K.lactis* VP2T (results not shown). The void volume fraction of pYELC5.PO contains fully processed VP3 showing that its presence in the void volume is not due to unprocessed precursor polyprotein. The extent of breakdown is quite extensive in the included volume fractions of the *S.cerevisiae* products.

It would thus appear that in both *E. coli* and yeast, undegraded VP2 tends to be present primarily in a high molecular weight aggregated form.

All the above results with yeast constructs were obtained with yeast cells treated with zymolyase to convert them to spheroplasts, followed by a brief sonication. This method took up to two hours and led to the release or activation of cellular proteases. In an alternative procedure, the extent of proteolytic degradation can be minimized by rapid breakage (2 minutes) of cells with glass beads in a Braun Homogenizer, followed by separation of the high molecular weight aggregate from soluble proteins (including proteases) by gel-filtration or sedimentation. The presence of protease inhibiors such as PMSF and the lowering of pH during extraction may also be used to minimize degradation of VP2.

EXAMPLE 5

Immunogenicities of the void volume and included volume fractions.

The included volume fractions from the yeast constructs and *E. coli* pTTQ18.VP2 were non-immunogenic. On the other hand, the VP2 present in the void volume of all the yeast constructs, but not *E. coli* pTTQ18.VP2, was highly immunogenic (Table 4). Thus, yeast-derived VP2 present in a high molecular weight aggregated form, but not its *E. coli* counterpart, produces a protective immune response in chickens.

TABLE 4

Testing immunogenicity of viral and recombinant IBDV antigens that eluted in either the void or included volumes, after fractionation on a sephacryl S-300 column, by determining serum antibody levels six weeks after immunisation of SPF birds.

| CONSTRUCT | COLUMN FRACTION | EIA TITRE | VN TITRE |
| --- | --- | --- | --- |
| pTTQ18.VP2 | void | 100 | <100 |
|  |  | 100 | <100 |
|  | included | <50 | <100 |
|  |  | <50 | <100 |
| pYELC5.POΔXhoI | void | 25,600 | 6,400 |
|  |  | 25,600 | 1,600 |

TABLE 4-continued

Testing immunogenicity of viral and recombinant IBDV antigens that eluted in either the void or included volumes, after fractionation on a sephacryl S-300 column, by determining serum antibody levels six weeks after immunisation of SPF birds.

| CONSTRUCT | COLUMN FRACTION | EIA TITRE | VN TITRE |
| --- | --- | --- | --- |
|  | included | 200 | <100) |
|  |  | 200 | <100) |
| K. lactis VP2T | void | 25,600 | 2,560) |
|  |  | 12,800 | 1,280) |
|  | included | 50 | <100) |
|  |  | <50 | <100) |
| Viral VP2 | void | 51,200 | 51,200 |
|  |  | 51,200 | 51,200 |
|  | included | 50 | <100 |
|  |  | 200 | <100 |

EXAMPLE 6

Purification of Recombinant IBDV VP2.

Figure 8:
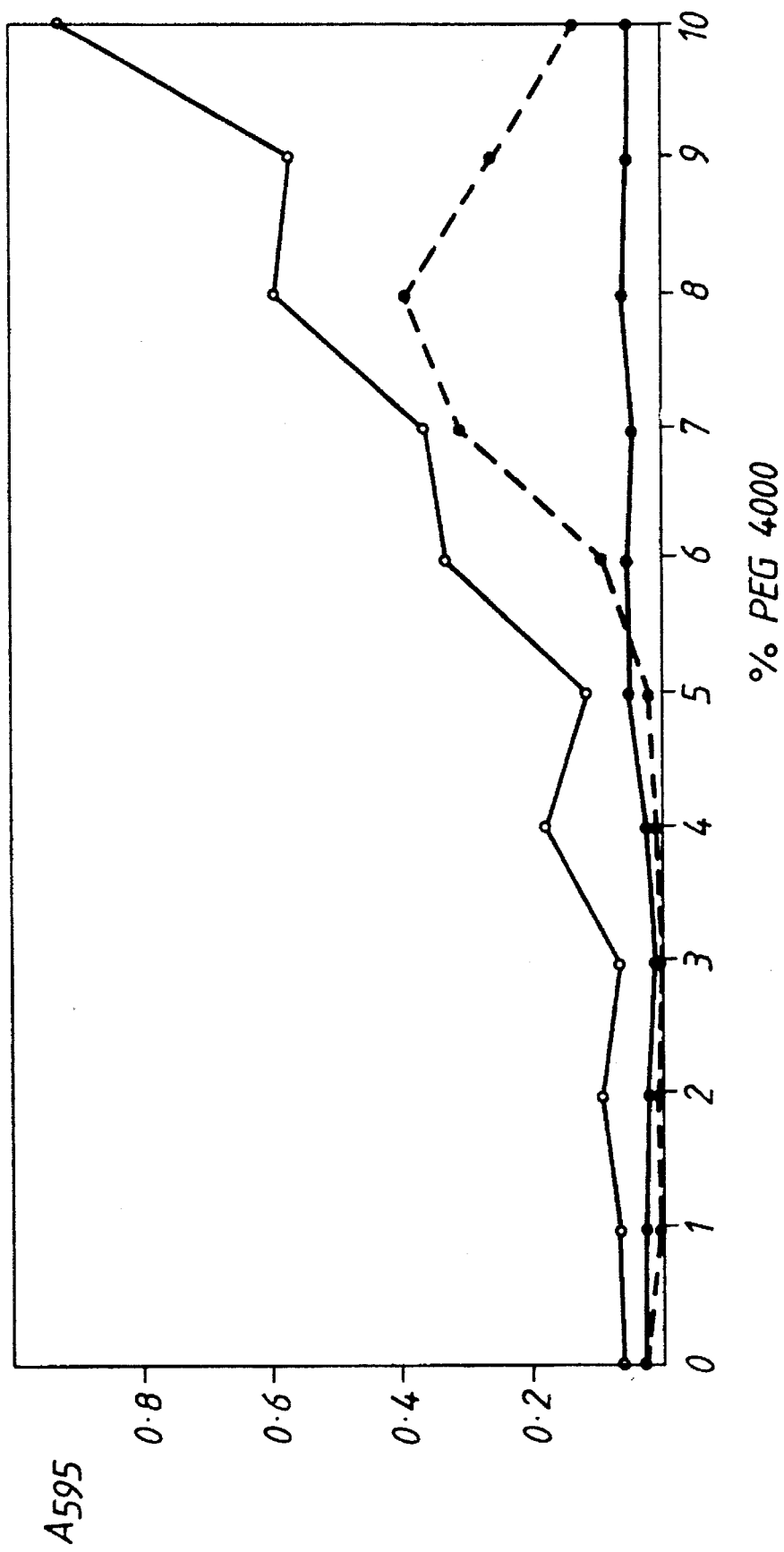
FIG. 8 shows proteolytic activity ($A_{595\ nm}$) of resolubilised pellets obtained following precipitation with PEG 4000. Aliquots of void sample (tubes 47–57, Fig.4); included sample (tubes 84–92, FIG. 4) and unfractionated 3K supernatant were mixed with PEG 4000, stored overnight at 4° C. and centrifuged at 2500 g. ■—■ void sample; ■---■ included sample; ○—○ 3K supernate.

Recombinant VP2 produced intracellularly in yeast is subject to proteolytic degradation, and the presence of some cellular proteins could lead to antigenic competition. It is, therefore, desirable to isolate the VP2 molecule in a form where it is both immunogenic and free of degradative proteases. Recombinant VP2 in yeast lysates is present in two forms—multimeric and monomeric. These forms can be separated by Sephacryl S300 gel permeation chromatography (Example 3). The multimeric form is less degraded (Example 4), and is highly immunogenic (Example 5). Most of the protease activity present in the yeast lysate elutes after this void volume fractions containing the multimeric VP2. This could account for the greater stability of the VP2 present in the void volume. Thus, gel-filtration effectively separates the multimeric and immunogen&c form of VP2 from the cellular proteases. The VP2 eluting in the void volume can be precipitated with 4% polyethylene glycol (PEG) 4000 2 C, 1 hour), The precipitate, which can be recovered by low-speed centrifugation (2000 g×10 min.), contains most of the VP2 activity (as assessed by reaction with NAb 39A) and is free of the majority of debradative proteases (FIG. 8). The monomeric form of VP2 eluting in the included volume is not precipitated at PEG concentrations of up to 10%.

The multimeric and immunogenic form of VP2 can also be recovered from the yeast 3K supernatant (without prior gel-filtration) by precipitation with 4% PEG as described above. As can be seen in FIG. 8, protease activity is precipitated in increasing quantities from the 3K supernatant as the PEG concentration is increased. At 4% PEG relatively little of the yeast protease is co-precipitated with VP2. The VP2 precipitate can be stably stored in 4% PEG, as at this and higher concentrations of PEG, protease activity appears to be inhibited.

Recombinant VP2 from yeast and *E. coli* can also be recovered in a multimeric and immunogenic form by using an aqueous two-phase system consisting of PEG and Dextran. Yeast lysates, obtained by glass-bead disruption in a Braun homogenizer, are made 7% in PEG 6000, 5% Dextran T500, 2M NaCl, 50 mM phosphate buffer pH 6.8, and incubated for 5 min. at RT. Low-speed centrifugation results in the formation of two phases separated by a distinct intraphase containing cell debris. The lower Dextran-rich phase contains the bulk of the cellular proteins and nucleic acids. The PEG-enriched upper phase contains relatively pure VP2 which can be recovered by incubation in the cold followed by low-speed centrifugation.

EXAMPLE 7

Restoration of the N-terminus of VP2 protein.

DNA sequences encoding the N-terminus of the IBDV polyprotein were restored by manipulation of the E. coli vector PO. The clone pEX.PO (Hudson et.al., 1986) contains coding information for all but the first five amino acids of the IBDV polypeptide that is encoded by the large dsRNA segment of IBDV. The vector pEX.PO was cut with NarI and XmaI cleaving out 3 kb of lacZ sequence. The remainder was fused together in the presence of T4 DNA ligase and duplexed oligonucleotides as shown. The resulting plasmids, p501 and p502, are 6 kb in size and differ from pEX.PO in having a 3 kb deletion. In place of the deletion they have inserted artificial oligonucleotide duplexes of less than 0.03 kb capable of encoding the first five amino acids (MTNLS-native, or MSNLS- yeast preferred) of the polyprotein.

The constructs were designed to maximize translation in yeast by having an optimal codon usage and an efficient translational initiator. As stated above, the oligonucleotides were synthesized in pairs as mixtures. In order to rapidly distinguish the oligonucleotides cloned, a further oligonucleotide, 3'OH TGT TAC TGA TTG A 5'OH was synthesized. This was kinased with radioactive ATP and hybridized to the DNA prepared from the clones. At 18° C. this oligonucleotide hybridized to all clones containing added duplexes, but at 30° C. only the perfect match remains hybridized.

Figure 9:
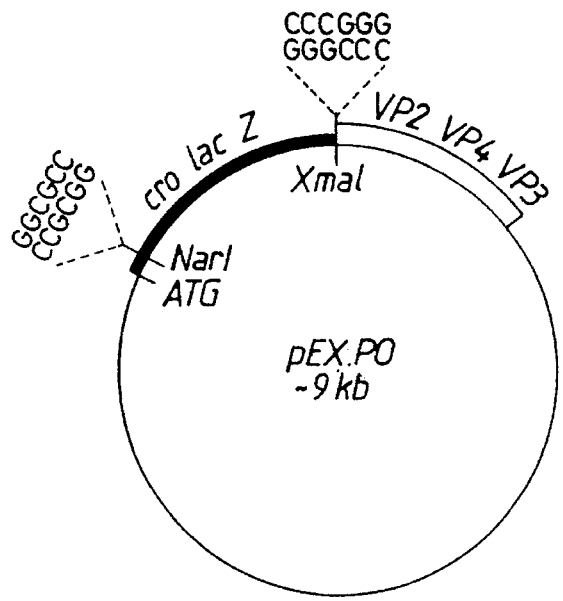
FIG. 9 shows the cloning strategy for the restoration of the N-terminus of the VP2 protein.
Figure 9:
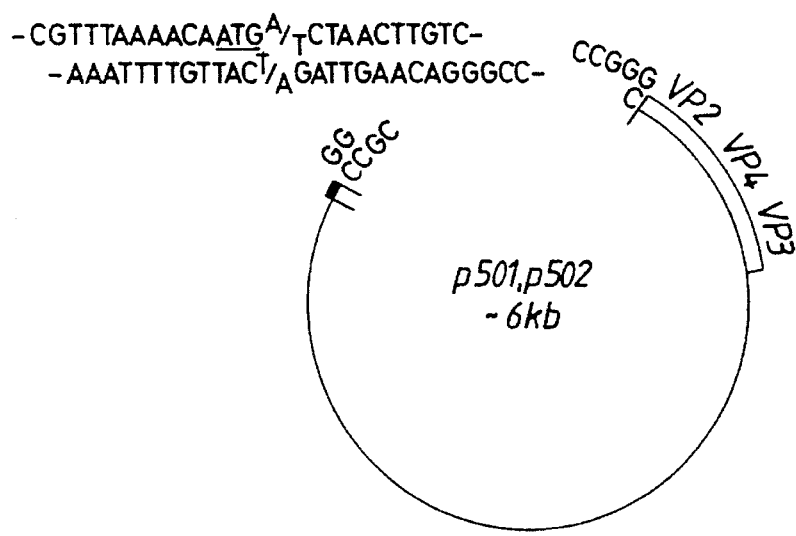

The constructs (p501 and p502) shown in FIG. 9 were formed directly from this process. They have four nucleotides too many but are suitable candidates for restoration of the reading frames. This was achieved in two steps, the first by cleaving these constructs with XmaI. The endonuclease XmaI cleaves the recognition sequence in duplex DNA CCCGGG, leaving single stranded ends 5'CCGG. Such ends were readily removed by treatment with the exonuclease Mung Bean Nuclease (Pharmacia) according to the procedure described by New England Biolabs. Following these treatments the cleaved vectors were intramolecularly religated to produce the in-frame constructs, p601 and p611 whose partial sequences, along with those of their parental vectors, are listed below.

DNA from p601 and p611 has been cloned into the yeast pAAH5 vector. The in-frame construct produces the polyprotein which is processed. The levels of VP2 synthesized are low (as expected from this non-regulated expression vector) but the VP2 appears stable unlike previously expressed VP2 using pAAH5.

EXAMPLE 8

Cloning and expression of the host protective antigen VP2 of IBDV variant strain Delaware E.

Two distinct serotypes of IBDV (I and II) exist (McFerran et.al., 1980; Jackwood et.al., 1982), and antigenic variants occur within serotype I (Saif et.al., 1987). Vaccination of breeder hens with recombinant VP2 from serotype I protects their offspring from IBDV infection, but a variant strain (Delaware E) resistant vaccination with serotype I inactivated vaccine has emerged. Inclusion of the variant strain into a commercial vaccine is highly desirable, as vaccination with a vaccine based on the escape mutant can protect against infection with the variant strain as well as the wild-type strain. Virus-neutralizing monoclonal antibodies recognize a conformation dependent discontinues epitope within 145 amino acid residues in the middle of VP2 (AccI-SpeI fragment) of strain 002-73 (PCT/AU88/00206). This epitope is changed in variant strain E as the virus-neutralizing MAb 39A does not react with vital proteins of strain E. VP2 of strain E has been cloned by constructing a cassette containing the immunogenic epitope and inserting it into expression vectors. This procedure could be used to clone and express the immunogenic fragments of any mutant which might arise in future, and would enable the quick incorporation of newly emerging variants into a vaccine formulation.

A. Materials and Methods (a) Isolation of the viral genomic RNA.

The genomic RNA of variant strain Delaware E (provided by Central Veterinary Laboratory, Weybridge, U.K.) was isolated from IBDV infected bursae as described previously (Azad et.al., 1985). A yield of 1.5 mg RNA was obtained from 70 g of bursae.

(b) Design of primers for cDNA synthesis and PCR amplification.

DNA fragments suitable for subcloning were obtained by cDNA synthesis and polymerase chain reaction (PCR) amplification of E-strain sequences using the genomic RNA as template and synthetic oligonucleotides containing homologies to VP2 as primers. At the 5' end of the primers restriction sites had been incorporated to facilitate the subcloning of the amplified fragments. Five different primers were synthesized which will allow the replacement of either the SmaI-XhoI, SmaI-SpeI, first AccI-XhoI or first AccI-SpeI fragments of VP2 from the type I Australian strain 002-73 with the corresponding fragments of VP2 from strain E or any other variant strain (Table 5).

| PO Constructs with Modified N-Termini | | | | | | | | | |
|---|---|---|---|---|---|---|---|---|---|
| Sequence of N-Terminal Region | | | | | | | | Frameshift | Clone Name |
| M | S | N | L | S | ? | D | Q | | |
| ATG | TCT | AAC | TTG | TCC | C GGG | GAT | CAA | +1 OR +4 | p501 |
| M | T | N | L | S | ? | D | Q | | |
| ATG | ACT | AAC | TTG | TCC | C GGG | GAT | CAA | +1 OR +4 | P502 |
| M | S | N | L | S | | D | Q | | |
| ATG | TCT | AAC | TTG | TCG | | GAT | CAA | in frame | p601 |
| M | T | N | L | S | | D | Q | | |
| ATG | ACT | AAC | TTG | TCG | | GAT | CAA | in frame | p611 |

(c) Synthesis of first strand cDNA from IBDV strain E.

Genomic RNA was denatured by boiling followed by snap freezing and used as the template for the synthesis of the first strand of complementary DNA by reverse transcriptase from avian myoblastosis virus (AMV RTase, Pharmacia). The synthesis was primed either by oligonucleotide N527 complementary to the N-terminus of VP2 (reaction A) to give the coding strand, or oligonucleotide N526 complimentary to the C-terminus (reaction B) to give the non-coding strand.

(d) PCR amplification of cDNA.

Figure 10:
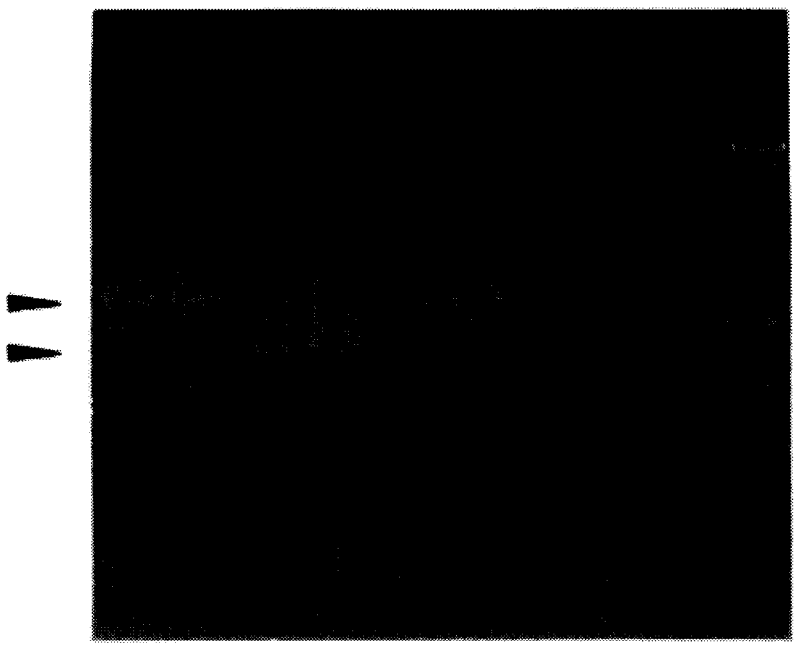
FIG. 10 shows agarose gel of PCR amplified DNA fragments.
Figure 11A:
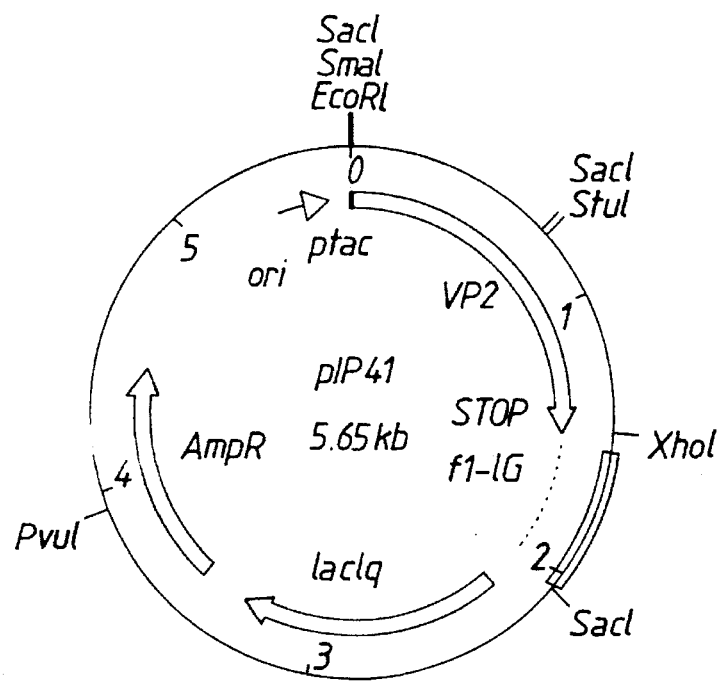
Figure 11B:
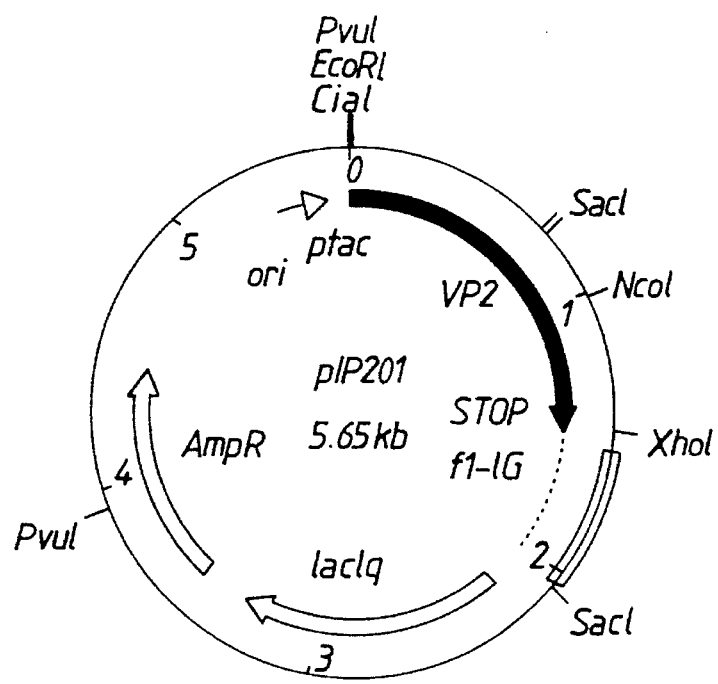
Figure 11C:
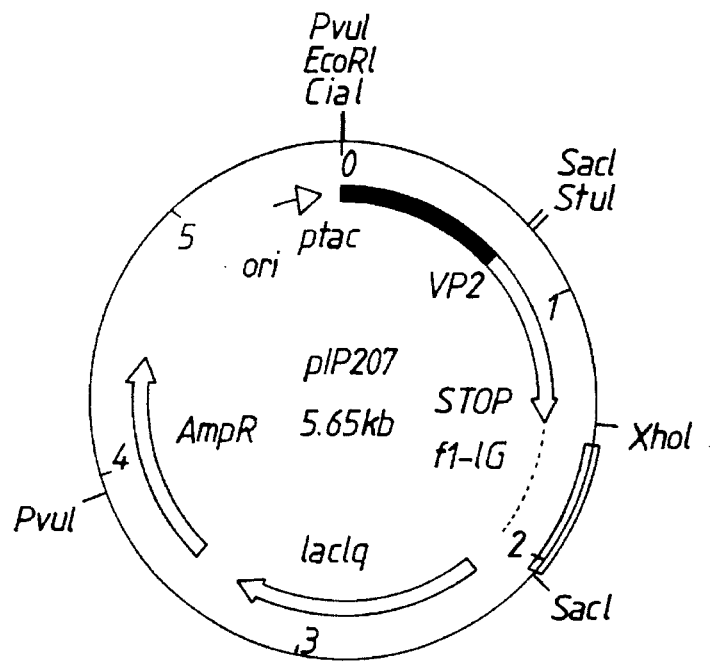
Figure 11D:
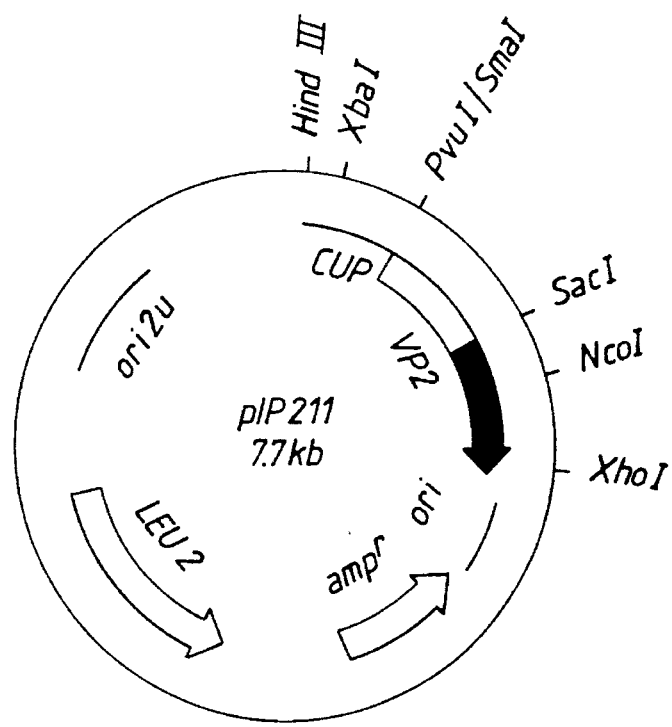

Specific sequences from the first strand cDNA were amplified by PCR after hydrolyzing the RNA from the RNA-cDNA hybrid. Oligonucleotides N527 and N526 complementary to the N-terminal and C-terminal region of VP2 were used as primers. In a control reaction oligonucleotide N526 was replaced by N533 complementary to the VP2 internal region at the SpeI site and N527 was replaced by N528 also binding to the N-terminal region of VP2. The PCR conditions used were, 30 cycles of denaturation at 95° C. for 1 min, annealing at 60° C,. for 1 min and extension at 72° C. for 2 min. The reaction products were phenol extracted, ethanol precipitated and analyzed by agarose gel electrophoresis (FIG. 10).

(e) Subcloning into *E.coli* expression and sequencing

The ends of the PCR amplified DNA were trimmed in a double digest with EcoRI and XhoI, and the resulting 1.5 kb fragment was cut out of an agarose gel and extracted with Geneclean (Bio 101). This fragment was then ligated with the 4.1 kb EcoRI-XhoI fragment of pIP41 (FIG.11) where it replaced VP2 of the Australian strain 002-73. The clone pIP201 containing VP2 from strain E was identified by restriction analysis and screening for VP2 expression in dot blots using monoclonal antibody (MAb) 6/1 that recognizes a linear epitope at the C-terminus of VP2a (Azad et.ai., 1987).

Plasmid pIP207 was constructed to give a hybrid VP2 consisting of the N-terminal half from strain E and the C-terminal half from strain 002-73 fused at the VP2 internal SacI site. This was done by replacing the 1.4 kb SacI fragments of pIP201 with the corresponding fragment from pIP41 (FIG. 11).

The M13 subclones for DNA sequencing were obtained by ligating restriction fragments of pIP201 into the appropriate sites in M13mp18 and M13mp19.

(f) Subcloninq into *S.cerevisiae* strain 6657-4D.

Clone pIP211 was constructed by subcloning the SacI-XhoI fragment containing the C-terminal half of VP2 from pIP201 into the yeast expression vector of pYELC5.POΔXhoI (FIG. 1c) where it replaced the corresponding region of the Australian strain 002-73. the plasmid was transformed into *S.cerevisiae* strain 6657-4D, and diploids were selected. *S. cerevisiae* clone pIP211 was analyzed for copper inducible VP2 expression. The VP2 hybrid in clone pIP211 contains a N-terminal half from strain 002-73 and a C-terminal half (carrying the regions specific for MAb 39A binding) from strain E. The hybrid protein is fused at the SacI site within VP2. There are no amino acid changes in the N-terminal halves of the VP2 molecules from different IBDV strains. The presence of E-VP2 DNA in these constructs has been confirmed by restriction analyses.

(g) DNA sequencing.

Double-stranded sequencing and single-stranded sequencing of recombinant pIP201 or M13 clones was carried out using either the T7 polymerase (Pharmacia) or the Taq polymerase system (Promega), according to the manufacturer's instructions, with either the universal sequencing primer supplied in the kits or synthetic oligonucleotides based on sequences of IBDV strain 002-73.

(h) Expression and characterization of recombinant protein.

Plasmids were maintained in *E. coli* DH5a (BRL) in LB medium containing 0.4% glucose and 100 μg/ml ampicillin. The expression of VP2 under the control of the Taq promoter was induced by growing for 2 h in the same medium containing 0.5 mM IPTG but omitting glucose.

In yeast the expression of VP2 from the CUP1 promoter was induced by adding 0.5 mM $CuSO_4$ to YNB 2% glucose medium and growth for 2 h at 30° C.

Bacteria were lysed by lysozyme treatment and sonication. Yeast cells were lysed in a Braun homogenizer.

Proteins were analyzed by dot blots, SDS PAGE, and Western blots.

B. Results and Discussion.

The host protective antigert VP2 of variant strain E of IBDV has been cloned from genomic RNA using oligonucleotides complementary to conserved regions as primers for PCR. The amplification of the correct fragment was based on the finding that changes between strains 002-73 and E must have occurred in the middle of VP2 (AccI-SBeI region) which forms the virus-neutralizing conformational epitope. The virus neutralizing MAb 39A does not recognize proteins of variant strain E.

(i) Cloninq

The specificity of the primers for VP2 sequences in the synthesis of cDNA and the PCR could be shown by obtaining fragments of the expected size when different primers were used. Only VP2 specific DNA sequences were amplified. In a reaction containing primers N527 and N526 a 1.5 kb fragment corresponding to full length VP2 was amplified, whereas in a control reaction where primer N526 homologous to the VP2 C-terminus had been substituted with primer N533 homologous to the region around the SpeI site (amino acid residue 350), a smaller fragment of only 1 kb was synthesized as expected (FIG. 10).

The ends of the amplified 1.5 kb full length VP2 fragment could be trimmed with EcoRI and XhoI. When the fragment was inserted into the corresponding sites of pIP41, replacing VP2 of the Australian strain 002-73, those sites were maintained and in addition the ClaI and PvuI sites present in the primer were incorporated. The correct clone pIP201 was confirmed by restriction analysis with ClaI and PvuI.

The differences in the N-terminus of VP2 from piP41 and pIP201 are shown in Table 7.

(ii) DNA sequence.

The SacI-SpeI region of strain E containing the virus-neutralizing epitope has been sequenced and the resulting amino acid sequence was compared to the sequence of strain 002-73 (Hudson et.al., 1986). Both strains differ in 15 amino acid residues within the SacI-SpeI fragment (Table 9). The most striking features of the changes in variant E were a G317D and D322E substitution in strain E in the region of the second hydrophilic peak. The E strain also contained a new unique NcoI restriction site and had lost the StuI site present in 002-73 allowing the convenient discrimination between 002-73 and E strain DNA sequences.

(iii) Expression.

Recombinant VP2 of strain E could be expressed from pIP210, but its binding to monoclonal antibodies (MAbs) 9/6 and 6/1 was weaker than with VP2 of the Australian strain expressed from pIP41 (FIG. 9). When assayed in dot blots with MAbs 6/1 and 9/6 the reactivity was only approx. 1/5, and reactivity with MAb 39A was lost completely. VP2 of pIP210 and pIP41 differ in their N-terminus (Table 7)

which might contribute to a reduced expression level or reduced stability in pIP201. To solve the question whether this difference is important or whether the expression levels are the same in both plasmids and only the epitopes are altered and account for reduced binding, VP2 hybrid proteins between Australian and E strain have been constructed and their reactivity with MAbs was compared on dot blots (FIG. 12).

Plasmid pIP207 contains a hybrid VP2 consisting of the N-terminal half from strain E and the C-terminal half from strain 002-73 fused at the VP2 internal SacI site. In plasmid 211 the order is reversed and the N-terminus of VP2 consists of sequences from strain 002-73, and the C-terminus from strain E.

The binding of the hybrid VP2 from pIP207 containing the modified N-terminus to MAbs 39A, 9/6 and 6/1 is the same as with pIP41 and much stronger than with pIP210 (FIG. 9). This means that the expression levels of VP2 in pIP41, 201, 207 and 211 are not influenced by differences in the N-terminus, and only changes in the epitopes are contributing to differences in the reactivity with MAbs.

Comparison of the binding activity of plasmids pIP207 and 211 leads also to the conclusion that the residues involved in the formation of the conformational virus-neutralizing epitope which is recognised by MAbs 39A and 9, is localized distal to the SacI site in the middle of VP2. The hybrid VP2 produced by pIP211 is therefore a promising candidate for a recombinant IBDV vaccine against variant strain E. The hybrid VP2 from pIP211 has the same expression levels as the Australian strain 002-73 VP2 and contains the epitopes characteristic for variant E. Chickens vaccinated with hybrid VP2 of pIP211 expressed in yeast produced antibodies neutralize IBDV strain 002-73 (see Table 9).

TABLE 5

Design of primers for cDNA synthesis and PCR amplification.

| | | EcoRI | PvuI | ClaI | | | | | |
|---|---|---|---|---|---|---|---|---|---|
| N527: | 5'ATATAT | GAAT | TCGATCGCAT | CGATGACAAA | CCTGTCAGAT | CAAACCCAGC | AG3' |
| | | >>>>>>>>* | | >>>>>>>>>> | >>>>>>>>>> | >>>>>>>>>> | >> |
| | | | | M    1T | | 5D | |
| | SmaI | BamHI | | | | | |
| N528: | 5'TTAA | CCCGGG | GATCCAACCC | AGCAGATTGT | TCCGTTTATA | CGGAGCC 3' |
| | | >>>> | >>>>@>>>>> | >>>>>>>>>> | >>>>> | >>>>>>> |
| | | | 5D | | | | |
| | BamHI | AccI | | | | | |
| N531 | 5'TTAA | GGATCC | GTCTACACCA | TAACTGCCGC | AGATGATTAC | CAATTCTC 3' |
| | | >>>>>>>>>> | >>>>>>>>>> | >>>>>>>>>> | >>>>>>>> |
| | | | PstI | XhoI | | | |
| N526: | 5'TTAA | CTGCAG | GCTCGAGCAG | TTCCTGAAGC | GGCCTGGGCC | TCATCGCCC3' |
| | | > >>>>>>>>> | >>>>>>>>>> | >>>>>>>>>> | >>>>>>>>> |
| | HindIII | SpeI | | | | | |
| N533: | 5'TTAA | AAGCTT | GGCTACTAGT | GTGACGGGGC | GGAGGGCACC3' |
| | | >>>>>>>>>> | >>>>>>>>>> | >>>>>>>>>> |

Restriction sites (underlined) were incorporated at the 5' end of the primers to enable convenient cloning of the PCR amplified fragment. Nucleotides complementary to sequences of IBDV from strain 002-73 are marked by arrows (>>>). In N527, N528 and N531 the VP2 homologeous region is complementary to the non-coding strand, and in N526 and N533 complimentary to the coding strand of IBDV. In N527 the asterix (*) marks the G>T nucleotide substitution introduced to create the ClaI site, and the ATG initiation codon forming part of the ClaI site is shown in bold. In N528 the @ marks the A>C substitution to create the BamHI site. The corresponding amino acid residues of the coding strand are shown below the DNA sequence.

TABLE 6

N-terminal fusions of VP2 to the multiple cloning region.

pIP41 (002-73 IBDV)

```
                                      5
 M   N   S   S   S   V   P   G   D   Q   T
ATG AAT TCG AGC TCG GTA CCC GGG GAT CAA ACC ... VP2
--------         --------         --------
                 --------         --------
    EcoRI        SacI      KpnI    SmaI
``` pIP201 (E IBDV)

```
                                 1               5
 M   N   S   I   A   S   M   T   N   L   S   D
ATG AAT TCG ATC GCA TCG ATG ACA AAC CTC TCA GAT ...
--------         --------
                 --------
    EcoRI  PvuI    ClaI
```

Both constructs contain a modified N terminus. Sequences corresponding to VP2 are printed bold. The numbers correspond to the residues in the native protein. VP2 of pIP41 begins with eight residues from the vector fused to residue 5Asp of VP2. In pIP201 six residues from the primer precede the Met start codon of VP2.

TABLE 7

Expression of recombinant VP2.

| | | Dot blots with MAb's | | |
|---|---|---|---|---|
| VP2 from | plasmid | MAb39A | MAb9/t | MAb6/t |
| *E. coli* | | | | |
| 002-73 | pIP41 | +++ | +++ | ++ |
| E | pIP201 | – | + | + |
| E/002-73 | pIP207 | +++ | +++ | ++ |
| Yeast | | | | |
| 002-73 | pYELC5-VP2 | +++ | +++ | ++ |
| 002-73/E | pIP211 | – | + | + |

TABLE 8

Amino acid sequences of AccI-SpeI region of IBDV strains 002-73 and E.

| | AccI 205 | 210 | | 220 | | 230 | | 240 | SacI | StuI 250 |
|---|---|---|---|---|---|---|---|---|---|---|
| E | | | TSL | | | | | SVGGE | LVFKT | SVQSL |
| 002-73 | YTITA | ADDYQ | FSSQY | QPGGV | TITLF | SANID | AITNL | SVGGE | LVFQT | SVQGL |
| hydrophil | | | | | | | | | | |
| | | 260 | | 270 | | 280 | | 290 | | 300 |
| E | VLGAT | IYLIG | FDGTA | VITRA | VAANN | GLTAG | IDNLM | PFNLV | IPTNE | ITQPI |
| 002-73 | VLNAT | IYLVG | FDGTT | VTTRA | VAAGN | GLTAG | TDNLM | PFNLV | IPTSE | ITQPV |
| | | | | | | | | | SpeI | |
| | | 310 | | 320 | | 330 | | 340 | | |
| E | TSIKL | EIVTS | KSDGQ | AGEQM | SWSAS | GSLAV | TIHGG | NYPGA | LRPVT | |
| 002-73 | TSIKL | EIVTS | KSGGQ | AGDQM | SWLAS | GNLAV | TIHGG | NYPGA | LRPVT | |
| hydrophil | | | | | | | | | | |

TABLE 9

Cross protection against the Australian strain 002-73 by immunization with VP2 epitope from variant E.
Chicken serum antibody response to vaccination with recombinant hybrid VP2 (N-terminal half from strain 002-73 and C-terminal half containing the virus-neutralizing epitope from variant strain E) from pIP211.

| YEAST LYSATE FROM pIP211 PREPARATION | ANTIBODY TITRE AT | | | | | |
|---|---|---|---|---|---|---|
| | WEEK 0 | | WEEK 4 | | WEEK 6 | |
| | ELISA | VN | ELISA | VN | ELISA | VN |
| 3k Supernatant | 50 | <10 | 6400 | 640–1280 | 6400 | 640–1280 |
| | 50 | <10 | 1680 | 40–80 | 1600 | 40–80 |
| 12k Supernatant | <50 | <10 | 6400 | 640 | 6400 | 640 |
| | <50 | <10 | 6400 | 5120 | 12800 | 1280–2560 |

NOTE:
ELISA titres and VN (virus-neutralising) titres are against the Australian 002-73 strain.

EXAMPLE 9

Identification of residues involved in the binding of monoclonal antibodies to the virus-neutralizing epitope.

Virus-neutralizing monoclonal antibodies recognize a conformation dependent discontinues epitope within 145 amino acid residues in the middle of VP2 (AccI-SpeI fragment) (PCT/AU88/00206). This fragment consists predominantly of very hydrophobic residues but also contains two small hydrophilic stretches close to either end. Previous studies involving deletion-expression analyses, suggested that the two hydrophilic peaks may be important determinants in the formation of the conformational epitope (PCT/AU88/00206 and Azad et.al., 1987). Thus the site-directed mutations were concentrated in these areas. However the importance of the intervening hydrophobic region was also examined.

Variant strain E, which is resistant to vaccination with serotype I inactivated vaccine and has lost the ability to bind to monoclonal antibody 39A specific for the virus-neutralizing conformational epitope proved to be valuable to identify the residues important for MAb 39 binding.

A. Materials and Methods.

1. Construction of DIP41 for mutagenesis and expression of VP2.

VP2 (of strain 002-73) was subcloned as a 1.5 kb SmaI-XbaI fragment from plasmid pEX.POΔXhoI-PstI into the SmaI-XbaI sites of pTTQ18(Amersham) to give pTTQ18-VP2. The small DraI-SalI fragment was then deleted to remove the lacZu fragment and a 12-met BamHI linker (Pharmacia) and the f1 intergenic region from pUC-f1 (Pharmacia) were inserted at that position to give in pIP41. Expression of VP2 is under control of the tac promoter and single stranded DNA can be obtained using M13 helper phage.

2. Site directed mutauenesis.

Single amino acid substitutions and deletions were produced by oligonucleotide directed mutagenesis of a single-stranded DNA template obtained from phagemid vector piP41 (or piP201 for the back-mutation of VP2 from strain E). Mutations were generated with the "dut ung" method or by using the Amersham mutagenesis kit. Amino acid insertions were created by introducing linkers into the unique StuI site in pIP41.

3. Screening and characterization of mutants.

The oligonucleotides used in the single amino acid substitutions were engineered so that they introduced new restriction sites into the plasmid to enable easy identification. The linker inserts were also screened by restriction enzyme digestion. All mutants were sequenced by double-stranded DNA sequencing to confirm the expected substitutions and insertions.

The phenotype of the mutants was analyzed using three different monoclonal antibodies (MAbs) 9/6, 39A and 6/1. Cell lysates were assayed by immunoblotting and compared to the wild-type. MAbs 9/6 and 39A recognize the 145 amino acid region of VP2. MAb6 binds to an area outside AccI-SpeI at the C-terminal end of VP2 and was used to detect non-specific changes in the protein caused by the mutants.

B. Results and Discussion.

(A) Mutagensis within AccI-SDeI region.

Conservative and non-conservative changes were introduced into The hydrophilic regions on either end of the AccI-SpeI region and the contribution of the hydrophobic region between those hydrophilic peaks was probed by linker insertion at the StuI site. The effect of the mutations on MAb binding was analyzed by dot blotting. Substitution of the charged residues in the first hydrophilic peak to neutral residues had no influence on the binding of MAbs (Table 10).

The insertion of four amino acids (either Pro Asp Pro Gly in pIP39, or Leu Thr Leu Thr in pIP47) into the hydrophobic region at the StuI site around residue 253 in VP2, specifically prevented the binding of MAbs 39A and 9/6. This region is therefore either part of the epitope or specifically involved in the formation of the epitope, as MAb 6/1 binding was not affected (Table 10).

Residues in the second hydrophilic region close to the SpeI site around aa 300–320 are also important for the formation of the conformational epitope. A 23 residue deletion in pIP77 led to the loss of binding to MAb 39A and 9/6, but not MAb 6/1. Non-conservative single amino acid substitutions (Lys308Ala and Lys315Ala) in this region destroyed the conformation and led to an instability of the protein as MAb 6 binding was also affected. The conservative substitution Lys315Arg had no measurable effect on MAb binding.

(b) Differences in the epitope of variant E.

The MAb 39A which recognizes the conformational epitope in VP2 of strain 002-73 does not recognize VP2 of variant strain E. Residues responsible for the differences in the conformational epitope between the Australian strain 002-73 and variant strain E, have been localised distal to the SacI site in the C-terminal half of VP2. This has been shown by creating VP2 hybrid proteins between the Australian strain and variant E (see previous Example 8, FIG. 11) and analysing the binding of the products to MAbs in dot blots (see previous Example 8, FIG. 12). Dot blots of hybrid VP2 from plasmids piP207 (E/002-73 ) and piP211 (002-73 /E) with MAb 39A showed that the C-terminal half determines the phenotype characteristic for each strain (Table 11; for details of plasmids see in previous Example 8, FIG. 11).

The amino acid sequence of the AccI-SpeI fragment of VP2 from variant strain E was compared with the corresponding fragment of the Australian strain 002-73. Between both strains only 14 residues are different in the 105 amino acid long SacI-SpeI fragment, and of those only two substitutions (317Asp and 322Glu in strain E compared with 317Gly and 322Asp in strain 002-73 ) occurred in the second hydrophilic peak (see previous Example 8, Table 8). The mutation of the single residue 322Glu in the second hydrophilic peak of VP2 from strain E in pIP201 to 322 Asp as in the sequence of the Australian strain, was sufficient to restore the binding to the virus-neutralizing MAb 39A to the same level as in the 002-73 strain (Table 11). This residue is essential for the conformational epitope as serogroup specificity can be converted by a single bp change in this position.

C. Conclusions

Within the AccI-SpeI fragment two regions contributing to the formation of the virus neutralizing conformational epitope have been were identified by site directed mutagenesis. Residues in the hydrophobic region at the StuI site, and residues in the second hydrophilic region close to the SpeI site, are specifically involved in the formation of the epitope recognised by MAbs 9/6 and 39A.

Residues contributing to the differences in the conformational epitope between strains 002-73 and variant E, and involved in binding to MAbs, have been localised distal to the SacI site in VP2. The back-mutation of a single residue 322Glu in strain E to 322Asp as in the sequence of the Australian strain was sufficient to restore the binding to the virus-neutralizing MAb 39A.

TABLE 10

Results of site directed mutagenesis in pIP41.

| Plasmid | Mutation | Phenotype in dot blots | | |
|---|---|---|---|---|
| | | MAb9/6 | 39A | 6/1 |
| pIP41 | wild type | + | + | + |
| First hydrophilic peak | | | | |
| pIP6 | Asp211Glu | + | + | + |
| pIP64 | Asp211Ala | + | + | + |
| pIP63 | Asp212Ala | + | + | + |
| Second hydrophilic peak | | | | |
| pIP66 | Lys308Ala | − | − | − |
| pIP69 | Lys315Ala | −/+ | −/(+) | −/+ |
| pIP70 | Lys315Arg | + | + | + |
| pIP77 | 298–321(23aa del.) | − | − | + |
| pIP75 | [deletion B] | − | − | + |
| Intermediate hydrophobic region | | | | |
| pIP39 | 253(+PDPG)254 | − | − | + |
| pIP47 | 253(+LTLT)254 | −/(+) | − | + |

TABLE 11

Expression of recombinant VP2.

| VP2 from | plasmid | Dot blots with MAb's | | |
|---|---|---|---|---|
| | | MAb39A | MAb9/6 | MAb6/1 |
| | E. coli | | | |
| 002-73 | pIP41 | +++ | +++ | ++ |
| E | pIP201 | − | + | + |
| E/002-73 backmutation of E (pIP201) | pIP207 | +++ | +++ | ++ |
| D317G E322D | pIP203 | +++ | +++ | + |
| E322D | pIP204 | +++ | +++ | + |
| | Yeast | | | |
| 002-73 | pYELC5-VP2 | +++ | +++ | ++ |
| 002-73/E | pIP211 | − | + | + |

EXAMPLE 10

Transfer of maternal antibodies to eggs and progeny chickens of vaccinated hens.

Adult SPF White leghorn chickens were vaccinated twice at an interval of 8 weeks with 45 µg of recombinant protein in Freund's incomplete adjuvant. The hens were artificially inseminated (AI) and fertile eggs collected. Yolk antibody was determined in eggs collected 3 to 6 weeks post-secondary vaccination by extraction with chloroform and reconstitution to their original volume. The titres of antibody shown in Table 12 are the mean of 5 to 8 eggs from each hen. Chickens were hatched from the AI hens between 6 and 15 weeks post-secondary vaccination and bled from the wing at 3 days of age. The range of serum antibody levels in 10–15 chickens from each hen are shown in Table 12. All antibody titres were determined by ELISA.

The mean titre of antibody in the egg yolk was half to one quarter that in the circulation of the donor hen, while the titre of antibody in the circulation of the hatched chickens was variable (Table 12). The antibody induced in the hens by the recombinant subunit IBD vaccines was transferred via the yolk to the progeny chickens.

TABLE 12

Transfer of maternal anti-IBDV antibody to eggs and progeny chickens of hens injected with recombinant vaccines.

| Vaccine | Hen | Hen serum | Egg yolk (mean) | Chicken serum (range) |
|---|---|---|---|---|
| pYELC.5-PO | A | 409,600 | 204,800 | NA |
|  | B | 51,200 | 25,600 | NA |
|  | C | NA | 51,200 | 12,800–25,600 |
|  | A | NA | 102,400 | 12,800–25,600 |
| pYELC.5-PO▲XhoI | A | 102,400 | 25,600 | NA |
|  | B | 204,800 | 51,200 | NA |
|  | C | 51,200 | 25,600 | NA |
|  | A | NA | 25,600 | 12,800 |
|  | B | NA | 51,200 | 6,400–25,600 |
|  | C | NA | 12,800 | 3,200–12,800 |

EXAMPLE 11

Absorption of antiserum to native and recombinant VP2, with recombinant VP2.

To evaluate the antigenic relatedness of native VP2a/2b and recombinant VP2, various antisera were adsorbed a number of times with pYELC.5-PO▲XhoI. Aliquots of antisera (initially 100 µl) were mixed with an equal amount of pYELC.5-PO▲XhoI (20 µg/100 µl) and reacted at 37° C. for 1 hour. The antiserum was then centrifuged at 400,000 g/15 min. The antiserum was adsorbed in the same manner a further 3 times, with portions being taken at each step for titration by ELISA. The ELISA titre was adjusted for the dilution factor due to the additions of pYELC.5-PO▲XhoI.

Table 13 shows that recombinant VP2 removed most of the ELISA antibody from antisera to native VP2a/2b and to pYELC.5-PO▲XhoI. However, it removed a much smaller portion of the antibody to pYELC.5-PO.

Western blotting studies showed that the original and post-adsorption antiserum to pYELC.5-PO contained antibodies to VP3 which were not removed by adsorption with recombinant VP2. This finding also explains the finding in Example 14, that higher titres of ELISA antibody were required in chickens from hens vaccinated with pYELC.5-PO to protect them against IBDV (002-73), the higher titres reflecting antibodies to VP3.

TABLE 13

Absorption of antiserum to native and recombinant VP2, with recombinant VP2.

| | ELISA antibody titre after absorption number | | | | |
|---|---|---|---|---|---|
| Antiserum | 0[a] | 1 | 2 | 3 | 4 |
| Native VP2a/2b | 51,200 | 25,600 | 6,400 | 3,200 | 1,600 |
| pYELC.5-PO | 819,200 | 409,600 | 204,800 | 204,800 | 204,800 |
| pYELC.5-PO▲XhoI | 102,400 | 25,600 | 3,200 | 1,600 | 1,600 |

[a]Original titre of antiserum

EXAMPLE 12

Dose response of chickens to pYELC.5-PO▲XhoI.

Groups of four 6-week-old SPF White leghorn chickens were injected intramuscularly with 1.7 µg, 5 µg, 15 µg or 45 µg of pYELC.5-PO▲XhoI in Freund's incomplete adjuvant. The recombinant protein was contained in the 3K supernate fraction from the yeast cell lysate. The chickens were bled from the wing vein at 2-weekly intervals and the serum titrated for ELISA (A) and virus neutralizing (B) antibody. While the onset and magnitude of both the ELISA and neutralizing antibody responses were maximal with 45 µg dose, (FIG. 13) and minimal with the 1.7 µg dose, there was no significant difference between the serum antibody titres in the different treatment groups 6 weeks post-vaccination.

EXAMPLE 13

Serum antibody response of primed hens to pYELC.5PO▲XhoI.

Hens exposed to IBDV (002-73) at 10 weeks of age were injected intramuscularly with 45 µg of pYELC.5PO▲XhoI in Freund's incomplete adJuvant at 20 weeks of age. Both the virus neutralizing and ELISA antibody titres increased significantly by 2 weeks post-vaccination (FIG. 14), and the antibody titres remained elevated for at least a further 9 weeks. This experiment demonstrated that an oil adjuvant recombinant subunit vaccine is able to hyperimmunize primed hens, which is a common application of lnactivated IBD vaccines in commercial broiler breeding hens.

EXAMPLE 14

Minimum protective titre of maternal ELISA antibody in chickens hatched from artificially inseminated vaccinated hens.

Chickens hatched from SPF hens vaccinated twice with recombinant IBDV proteins, as outlined in Example 10, were challenged by the intraocular inoculation of 100 chick infectious doses of virulent IBDV (002-73), between 3 and 28 days of age. While the majority of chickens had titres of circulating maternal antibody ≧6400 and were completely protected from infection, as assessed by the absence of IBD vital antigen in their bursae 3 days post challenge, a number of chickens had lower titres of antibody at post-mortem and some of these were infected. This enabled the minimum protective titre of maternal antibody to be estimated from the number of chickens with a particular titre of antibody at post-mortem which resisted the challenge infection. For chickens hatched from hens vaccinated with pYELC.5-PO the minimum protective titre of ELISA antibody was approximately 1,600 (Table 14) while for chickens hatched from pYELC.5-POΔXhoI vaccinated hens the minimum protective titre was approximately 400 (Table 14). The latter value is comparable to that reported previously for progeny of hens vaccinated with a conventional inactivated oil-emulsion IBD vaccine (Fahey et.al., 1987). This indicates that the protective efficacy of the antibody induced by pYELC.5-POΔXhoI, as assessed by ELISA, is comparable to that to whole IBD virus. Conversely the protective ELISA titre of antibody to pYELC.5-PO is much higher than to pYELC.5-POΔXhoI or whole virus, possibly due to the presence of antibodies to VP3 (see Example 11).

TABLE 14

Minimum protective titre of maternal ELISA antibody in chickens hatched from vaccinated hens and challenged with IBDV.

| Hen Vaccination | Circulating maternal antibody following challenge | | | | | |
|---|---|---|---|---|---|---|
|  | 6400 | 3200 | 1600 | 800 | 400 | 200 |
| pYELC.5-PO | 0/15[a] | 0/3 | 2/7 | 5/6 | — | 3/3 |
| pYELC.5-POΔhol | 0/19 | 0/6 | 0/16 | 3/19 | 2/9 | 11/11 |

[a]Number of chickens infected/number of challenged chickens with a particular titre of maternal antibody when post-mortemed 3 days after challenge. All infected chickens had ELISA titres of IBDV antigen in the bursal ≧16. Groups of 5 age matched SPF chickens challenged with each groups of experimental chickens were uniformly susceptable to infection with IBDV.

REFERENCES

Azad, A. A., Barrett, S. A. and Fahey, K. J. (1985). *Virology* 143: 35–44.

Azad, A. A., Jagadish, M. N., Brown, M. A. and Hudson, P. J. (1987). *Virology* 161: 145–152.

Brown, F. (1986). *Intervirology*, 25,: 141–143.

Dobos, P., Hill, B. J., Hallet, R., Kells, D. T. C., Becht, H. and Teninges, D. (1979). *Journal of virology*, 32: 593–605.

Fahey, K. J., Crooks, J. K. and Fraser, R. A. (1987). *Aust.Vet.J.* 64: 203–207.

Hudson, P. J., McKern, N. M., Power, B. E. and Azad, A. A. (1986). *NuCleic Acids Res.* 14: 5001–5012.

Jackwood, D. F., Saif, Y. M. and Hughes, J. H. (1982) *Avian Diseases*, 26: 871–882.

McFerran, J. B., McNulty, M. S., McKilhop, E. R., Connor, T. J., McCracken, R. M., Collins, D. S. and, Allan, G. M. (1980). *Avian pathology*, 9: 395–404.

Saif, Y. M., Jackwood, H. D., Jackwood, M. W. and Jackwood, D. J. (1987). *Proceedings of the* 36th Western Poultry Disease Conference, 110–111.

We claim:

1. A plasmid encoding a recombinant IBDV VP-2 polypeptide, which is capable of inducing antibodies that passively protect chickens against infection by IBDV, comprising the native amino acid sequence of IBDV VP-2, wherein the five N-terminal amino acid residues of the native VP-2 sequence, MTLNS, have been replaced by the octapeptide MFSELDPQ.

2. A plasmid of claim 1 selected from the group consisting of pYELC5.PO, pYELC5.VP2T and pYELC5.POΔho1.

3. Plasmid pYELC5.PO.

4. Plasmid pYELC.5.VP2T.

5. Plasmid pYELC5.POΔXho1.

6. Plasmid pK.lactis.VP2T.

7. A host cell comprising a plasmid encoding a recombinant IBDV VP-2 polypeptide, which is capable of inducing antibodies that passively protect chickens against infection by IBDV, comprising the native amino acid sequence of IBDV VP-2, wherein the five N-terminal amino acid residues of the native VP-2 sequence, MTLNS, have been replaced by the octapeptide MFSELDPQ.

8. A *Saccharomyces cerevisiae* host cell comprising a plasmid selected from the group consisting of pYELC5.PO, pYELC5.VP2T and pYELC5.POΔXho1.

9. A *Saccharomyces cerevisiae* host cell comprising plasmid pYELC5.PO.

10. A *Saccharomyces cerevisiae* host cell comprising plasmid pYELC.5.VP2T.

11. A *Saccharomyces cerevisiae* host cell comprising plasmid pYELC5.POΔXho1.

12. A *Klulyveromyces lactis* host cell comprising plasmid pK.lactis.VP2T.

13. A recombinant IBDV VP-2 polypeptide, which is capable of inducing antibodies that passively protect chickens against infection by IBDV, comprising the native amino acid sequence of IBDV VP-2, wherein the five N-terminal amino acid residues of the native VP-2 sequence, MTLNS, have been replaced by an octapeptide selected from the group consisting of MFSELDPQ and MNSSSVPG.

14. A recombinant IBDV VP-2 polypeptide of claim 13 expressed in *Saccharomyces cerevisiae* by a plasmid selected from the group consisting of pYELC5.PO, pYELC5.VP2T and pYELC5.POΔXho1.

15. A recombinant IBDV VP-2 polypeptide expressed in *Saccharomyces cerevisiae* by plasmid pYELC5.PO.

16. A recombinant IBDV VP-2 polypeptide expressed in *Saccharomyces cerevisiae* by plasmid pYELC.5.VP2T.

17. A recombinant IBDV VP-2 polypeptide expressed in *Saccharomyces cerevisiae* by plasmid pYELC5.POΔXho1.

18. A recombinant IBDV VP-2 polypeptide expressed in *Kluveromyces lactis* by plasmid pK.lactis.VP2T.

* * * * *